(12) United States Patent
Cooper et al.

(10) Patent No.: US 11,564,854 B2
(45) Date of Patent: Jan. 31, 2023

(54) WHEELCHAIR PRESSURE ULCER RISK MANAGEMENT COACHING SYSTEM AND METHODOLOGY

(71) Applicants: University of Pittsburgh—Of the Commonwealth System of Higher Education, Pittsburgh, PA (US); The United States Government as represented by the Department of Veterans Affairs, Washington, DC (US)

(72) Inventors: Rory Alan Cooper, Gibsonia, PA (US); Chengshiu Chung, Pittsburgh, PA (US); Garrett G. Grindle, Pittsburgh, PA (US); Rosemarie Cooper, Gibsonia, PA (US); Sathish Andrea Sundaram, Pittsburgh, PA (US)

(73) Assignees: University of Pittsburgh—Of the Commonwealth System of Higher Education, Pittsburgh, PA (US); The United States Government as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 17/259,173

(22) PCT Filed: Jul. 11, 2019

(86) PCT No.: PCT/US2019/041327
§ 371 (c)(1),
(2) Date: Jan. 10, 2021

(87) PCT Pub. No.: WO2020/014430
PCT Pub. Date: Jan. 16, 2020

(65) Prior Publication Data
US 2021/0267826 A1 Sep. 2, 2021

Related U.S. Application Data

(60) Provisional application No. 62/696,414, filed on Jul. 11, 2018.

(51) Int. Cl.
*A61G 5/00* (2006.01)
*A61G 5/10* (2006.01)
(Continued)

(52) U.S. Cl.
CPC .......... *A61G 5/1091* (2016.11); *A61G 5/1043* (2013.01); *A61G 5/128* (2016.11);
(Continued)

(58) Field of Classification Search
CPC ...... A61G 5/1091; A61G 5/128; A61G 20/30; A61G 5/1043; A61G 2203/32; G16H 50/30; G16H 40/63
(Continued)

(56) References Cited

U.S. PATENT DOCUMENTS

| 6,030,351 A | 2/2000 | Schmidt |
| 6,287,253 B1 * | 9/2001 | Ortega ................... A61B 5/002 600/300 |

(Continued)

FOREIGN PATENT DOCUMENTS

| WO | WO-9825112 A2 * | 6/1998 | ............. B60N 2/002 |
| WO | WO9825112 A2 | 6/1998 | |

(Continued)

OTHER PUBLICATIONS

Crane, Barara A. et al, Responsiveness of the TAWC Tool for Assessing Wheelchair Discomfort, Disability and Rehabilitation: Assistive Technology, vol. 2, No. 2, pp. 97-103, 2007.
(Continued)

*Primary Examiner* — Brian L Swenson
*Assistant Examiner* — Hilary L Johns
(74) *Attorney, Agent, or Firm* — Bartony & Associates, LLC

(57) ABSTRACT

A wheelchair system includes a wheelchair including a plurality of force sensors including at least three force
(Continued)

sensors. A rigid seat pan is placed in contact with each the plurality of force sensors at a different position on the rigid seat pan so that the rigid seat pan does not contact the frame and forces on the rigid seat pan are transferred to the plurality of force sensors. Each of the plurality of force sensors is in communicative connection with a processor system. A memory system is in communicative connection and an interface system is in connection with the processor system and a user interface system in communicative connection with the processor system. Instructions stored on the memory system are executable by the processor system to determine a value of a variable related to a distribution of force on the rigid seat pan over time.

24 Claims, 16 Drawing Sheets

(51) Int. Cl.
    *A61G 5/12*         (2006.01)
    *G16H 20/30*       (2018.01)
    *G16H 50/30*       (2018.01)
    *G16H 40/63*       (2018.01)

(52) U.S. Cl.
    CPC ............ *G16H 20/30* (2018.01); *G16H 40/63* (2018.01); *G16H 50/30* (2018.01); *A61G 2203/32* (2013.01)

(58) Field of Classification Search
    USPC ........................................................ 280/647
    See application file for complete search history.

(56) References Cited

U.S. PATENT DOCUMENTS

| | | | | |
|---|---|---|---|---|
| 7,378,975 | B1* | 5/2008 | Smith ................... | A61B 5/1126 340/666 |
| 10,101,454 | B2* | 10/2018 | Pearlman ................ | G01S 17/89 |
| 2005/0083207 | A1* | 4/2005 | Smith .................... | A61F 5/3776 340/668 |
| 2015/0198440 | A1* | 7/2015 | Pearlman ................ | G01C 7/04 356/4.01 |
| 2015/0209207 | A1* | 7/2015 | Cooper .................. | A61G 5/128 701/49 |
| 2015/0351981 | A1* | 12/2015 | Sazonov .............. | A61G 5/1045 297/217.2 |
| 2016/0049062 | A1* | 2/2016 | Campbell ................ | A61G 5/10 340/573.1 |
| 2018/0042525 | A1* | 2/2018 | Sonenblum .......... | A61B 5/6894 |
| 2018/0108239 | A1* | 4/2018 | Pirio .................. | G08B 21/0461 |
| 2020/0405217 | A1* | 12/2020 | Jayaraman ............. | G16H 50/30 |

FOREIGN PATENT DOCUMENTS

| | | | | |
|---|---|---|---|---|
| WO | WO-2005107672 | A1 * | 11/2005 | ............. A61G 5/045 |
| WO | WO 2020014430 | | 1/2020 | |

OTHER PUBLICATIONS

Parmanto, Bambang et al., "iMHere: A Novel mHealth System for Supporting Self-Care in Management of Complex and Chronic Conditions." JMIR Mhealth and Uhealth vol. 1, issue 2, pp. 1-16 (2013).
Cooper R. A et al., The Relationship Between Wheelchair Mobility Patterns and Community Participation Among Individuals with Spinal Cord Injury, Assistive Technology, vol. 23, No. 3, pp. 177-183, 2011.
Worobey L et al., Increases in Wheelchair Breakdowns, Repairs and Adverse Consequences for People with Traumatic Spinal Cord Injury, American Journal of PM&R, pp. 463-469, vol. 91, No. 6, Jun. 2012.
Garber, Susan L. et al. Pressure Ulcer Prevention and Treatment Following Spinal Cord Injury: A Clinical Practice Guideline for Healthcare Professionals, Con Spinal Cord Clin Prac Guide, 2nd Ed, PVA, Washington, DC, 2014,pp. 1-85.
Makhsous M et al., Periodically Relieving Ischial Sitting Load to Decrease the Risk of Pressure Ulcers, Arch Phys Med & Rehabil, vol. 88, No. 7, pp. 862-870, 2007.
Ding D et al., Usage of tilt-in-space, recline, and elevation seating functions in natural environment of wheelchair users, J Rehabil Res & Dev, vol. 45, No. 7, pp. 973-984, 2008.
Schofield R et al., Reviewing the Literature on the Effectiveness of Pressure Relieving Movements, Nursing Research & Practice, vol. 2013 (2013), Article ID 124095, pp. 1-14.
Liu Hsin-Yi et al., A survey of feedback modalities for wheelchair power seat functions, IEEE Pervasive Computing, pp. 54-62, vol. 11, No. 3, Jul.-Sep. 2012.
Poropatich R.K et al., mCare: Using Secure Mobile Technology to Support Soldier Reintegration and Rehabilitation, Telemedicine and e-Health, vol. 20, No. 6, pp. 1-7, Jun. 2014.
Bert F et al., Smartphones and Health Promotion: A Review of the Evidence, J Med Syst (2014) 38:9995, pp. 1-11.
Ding D et al., Virtual coach technology for supporting self-care, PM&R Clinics of N Am, vol. 21, No. 1, 2010, pp. 179-194.
Hiremath S.V. et al., Development and evaluation of a gyroscope-based wheel rotation monitor for manual wheelchair users, J Spinal Cord Medicine (ISSN: 1079-0268), vol. 36, No. 4, pp. 347-356(10); Jul. 2013.
Bergstrom N. et al., Multi-site study of incidence of pressure ulcers and the relationship between risk level, demographic characteristics, diagnoses, and prescription of preventative interventions, J. American Geriatric Society, vol. 44, pp. 22-30, 1996.
Bevette G. et al., Best_practice protocols: Reducing harm from pressure ulcers, Nursing Management, vol. 38, No. 3, pp. 29-32, 2007.
Wu Y. K. et al., A Smart Phone Application for Improving Powered Seat Functions Usage: A Preliminary Study, Proceedings of the Rehabilitation Engineering and Assistive Technology Society of North America Conference, Seattle, Washington, USA, CD-Rom, Jun. 22-24, 2013, pp. 1-4.
Stockton L, Flynn M, Sitting and pressure ulcers 1: risk factors, self-repositioning and other interventions, Nursing Times, vol. 105, No. 24, 2009, pp. 1-9.
Chavez E. et al., Assessing the Influence of Wheelchair Technology on Perception of Participation in spinal cord injury, Arch Phys Med & Rehabil, vol. 85, No. 11, pp. 1854-1858, 2004.
Liu H et al., Case study: Pilot test of virtual seating coach evaluated by power seat function users, Proc of Rehabil Eng & Assistive Tech Soc N America Conference, Baltimore, MD, CD-ROM, Jun. 28-Jul. 3, 2012, pp. 1-5.
Garcia-Mendez Y, et al.. Health risks of vibration exposure to wheelchair users in the community, The J Spinal Cord Med, (ISSN: 1079-0268); vol. 36, No. 4, pp. 365-375(11); Jul. 2013.
Hong E-K. et al.. Comfort and stability of wheelchair backrests according to the TAWC, (toll for assessing wheelchair discomfort). Dis & Rehabil—Assist Tech, DOI: 10.3109/17483107.2014. 938365, 2014, pp. 1-5.
Fogg BJ, Hreha J, Behavior wizard: A method for matching target behaviors with solutions, Persuasive Technology, vol. 6137, pp. 117-131, 2010.
Cooper R.A. et al., Trends and issues in wheelchair technologies, Assist Tech, vol. 20, No. 2, pp. 61-72, 2008.
Rosser B. A, Eccleston C, Smartphone applications for pain management, Abstract, J. Telemedicine & Telecare, vol. 17, No. 6, pp. 308-312, Sep. 2011.
Hsin-Yi, Liu et al., Seating virtual coach: A smart reminder for power seat function usage, Abstract, Technology and Disability, vol. 22, No. 1-2, pp. 53-60, 2010.
Fogg BJ, Computers as Persuasive Social Actors, Persuasive Technology, No. 5, pp. 89-120, Dec. 2002.

\* cited by examiner

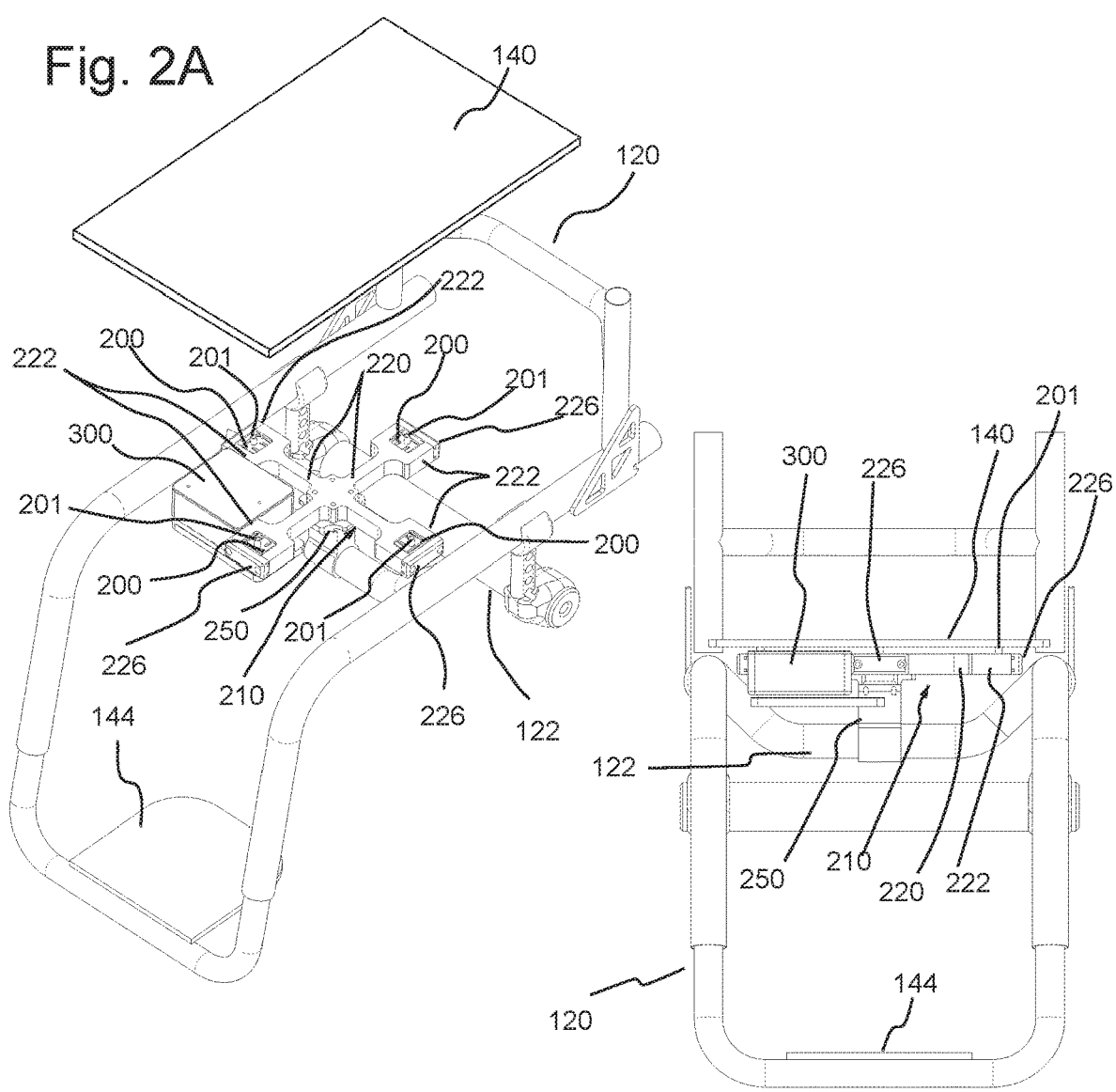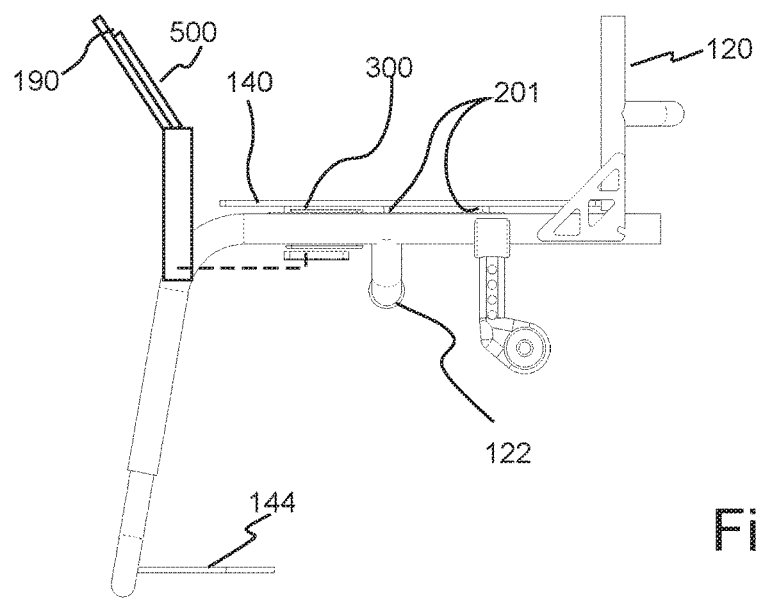

Table 1

| | Rater AK | Rater RC | Classifier (Complex Tree, 1Hz, win:60s) | Classifier (BaggedTree, 1Hz, win:60s) | KNN | SVM | Total |
|---|---|---|---|---|---|---|---|
| MW-VSC #1 | A | P | 1 | 1 | 0.011765 | 0 | 0.502941 |
| MW-VSC #2 | A | P | 1 | 1 | 1 | 1 | 1 |
| MW-VSC #10 | A | P | 1 | 1 | 1 | 1 | 1 |
| MW-VSC #13 | A | A | 1 | 1 | 1 | 1 | 1 |
| MW-VSC #14 | P | A | 0 | 0 | 0 | 0 | 0 |
| MW-VSC #16 | A | A | 1 | 1 | 1 | 0.588235 | 0.897059 |
| MW-VSC #17 | A | A | 1 | 1 | 1 | 1 | 1 |
| MW-VSC #18 | A | P | 0 | 0 | 0 | 0.641176 | 0.160294 |
| MW-VSC #19 | P | P | 1 | 1 | 1 | 1 | 1 |
| MW-VSC #20 | A | P | 1 | 1 | 0.925 | 0.654545 | 0.894886 |
| MW-VSC #27 | P | ?? | 1 | 1 | 1 | 1 | 1 |
| MW-VSC #35 | A | ?? | 0.814286 | 0.814286 | 1 | 1 | 0.814286 |
| MW-VSC #40 | P | ?? | 0.292857 | 0 | 1 | 0.492857 | 0.445429 |
| | Active: 5 Passive: 6 No data: 2 | Active 5 Passive: 5 No data: 3 | Active: 10 Passive: 3 | Active: 10 Passive: 3 | Active: 10 Passive: 3 | Active: 7 Passive: 2 Unknown: 4 | Active: 9 Passive: 2 Unknown: 2 |

Fig. 10B

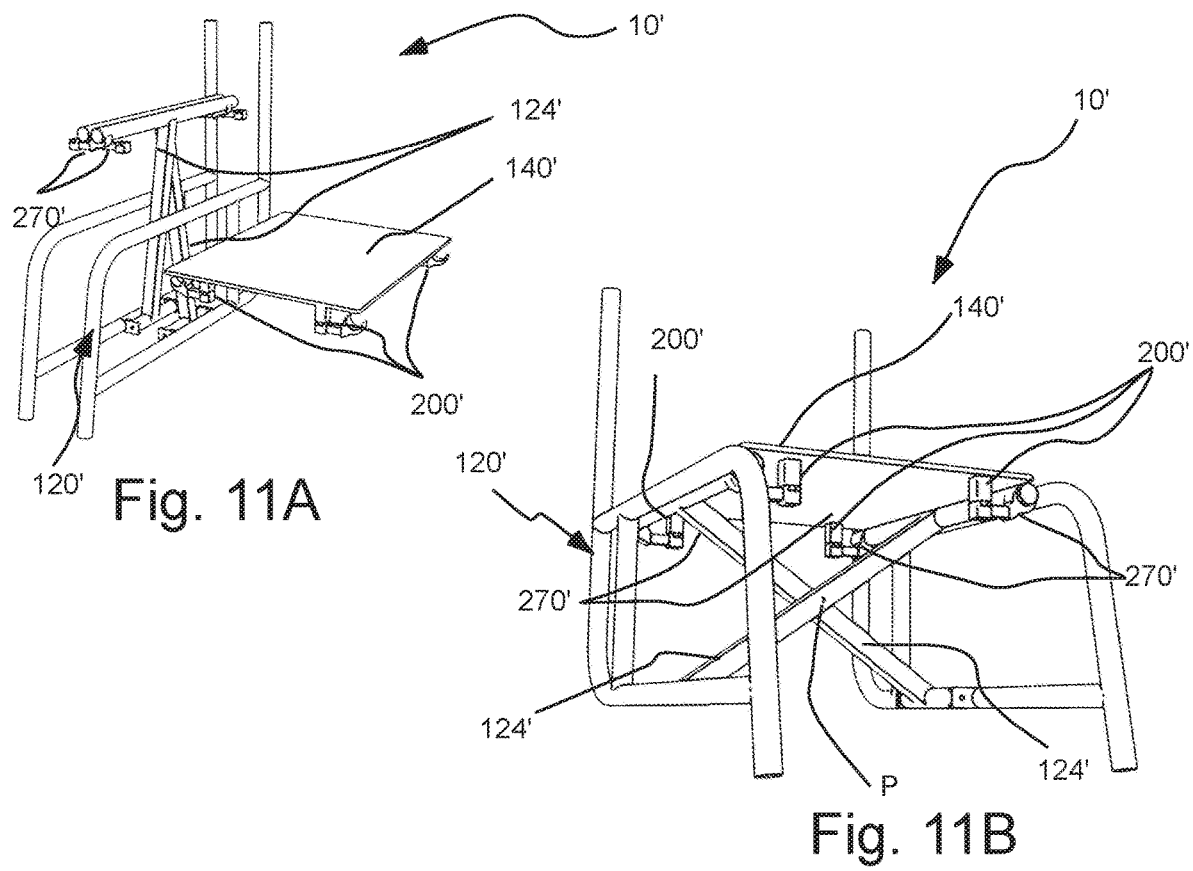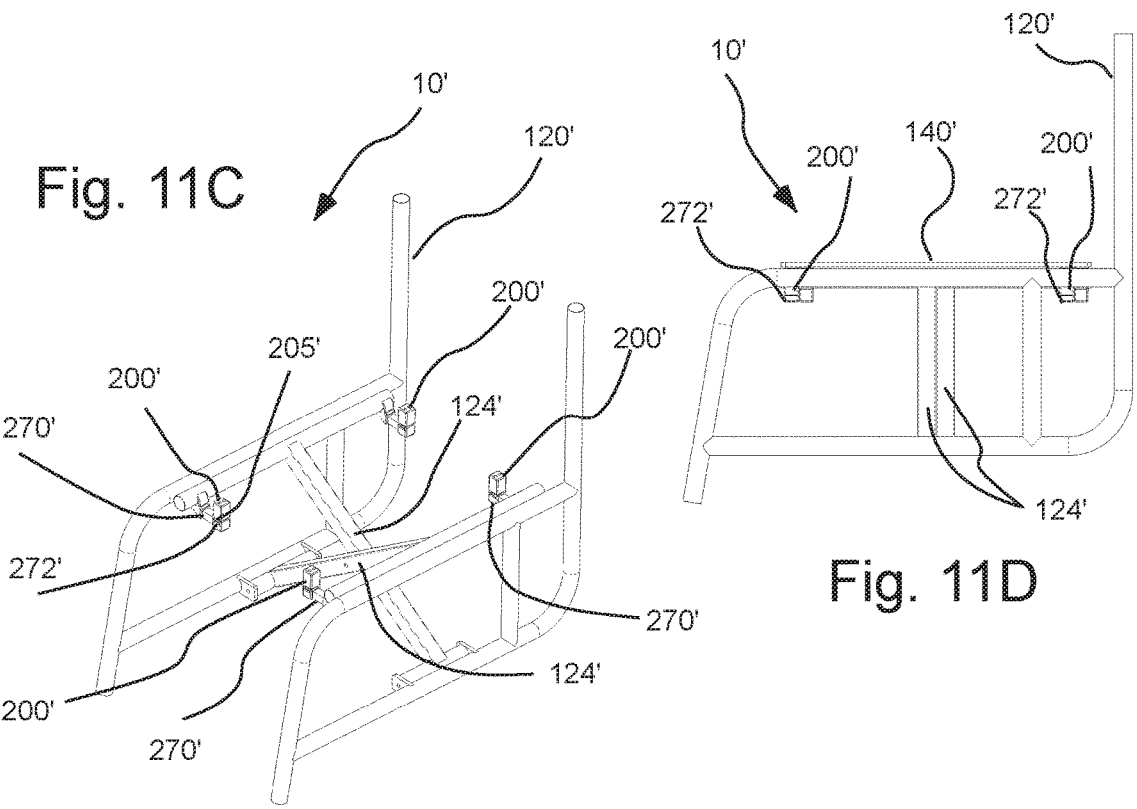

WHEELCHAIR PRESSURE ULCER RISK MANAGEMENT COACHING SYSTEM AND METHODOLOGY

CROSS-REFERENCE TO RELATED APPLICATIONS

This application is a national phase filing of PCT International Patent Application No. PCT/US2019/041327, filed Jul. 11, 2019, claims benefit of U.S. Provisional Patent Application Ser. No. 62/696,414, filed Jul. 11, 2018, the disclosure of which are incorporated herein by reference.

GOVERNMENTAL INTEREST

This invention was made with government support under grant no. W81XWH-17-1-0620 awarded by the Army Medical Research and Materiel Command and under grant no. 1449702 awarded by the National Science Foundation. The government has certain rights in the invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Proper training in use of wheelchairs has been identified as an important factor which may facilitate use in communities, and improve safety, user acceptance, and user satisfaction. However, training to perform pressure relief or dynamic repositioning is usually provided in a clinic with oral instructions with minimal practice because of limited interaction time. Furthermore, novice wheelchair users must learn how to operate and maintain their wheelchair, how to safely propel their chair, and how to perform pressure relief and repositioning sufficient to reduce risk of injury. The challenges of learning to manage seated pressure can be overwhelming for some individuals and requires frequent reinforcement.

Re-positioning for pressure relief is one important approach to reducing the risk of occurrence of pressure ulcers. However, with numerous activities and tasks happening every day, it is very easy to lose track of time and forget to perform pressure reliefs even when an individual is aware of the importance of pressure ulcer prevention. Wheelchair users may choose to ignore the need to perform pressure relief and stay in a fixed or static position for prolonged periods to accomplish tasks, trading potential health consequences for greater short-term participation. People tend to prefer options that are easy to process and bring instant outcomes.

People who are active sitters (that is, change their seated posture frequently) and/or who perform regular pressure relief (that is, lifting the buttocks off of the seat or significantly changing posture—by, for example, lying on the thighs) tend to be at lower risk for developing pressure ulcers. Educational tools (for example, user guides, oral instruction, web-sites, apps) have proven very effective in increasing the knowledge among manual wheelchair users of the risk of pressure ulcers but do little to improve compliance. Current reminders based on timers or simple pressure or contact switches have only proved modestly effective. Although there have been developments in studies for increasing compliance among electric powered wheelchair users who use power seat functions, there has been little research to develop technology interventions to promote positive behavioral changes among manual wheelchair users or users of powered wheelchairs without power seat functions to promote active sitting and regular pressure relief.

SUMMARY

In one aspect, a wheelchair system includes a wheelchair including a frame, a plurality of wheels attached to the frame and a sensor system including a plurality of force sensors. The plurality of force sensors includes at least three force sensors. Each of the plurality of force sensors is attached to the frame and is positioned at a different position (relative to the frame). A rigid seat pan is connected to or placed in (operative) contact with each the plurality of force sensors at a different position on the rigid seat pan so that the rigid seat pan does not contact the frame and forces on the rigid seat pan are transferred to the plurality of force sensors. The wheelchair system further includes a processor system. Each of the plurality of force sensors is in communicative connection with the processor system. The wheelchair system also includes a memory system in communicative connection with the processor system and a user interface system in communicative connection with the processor system. Instructions stored on the memory system are executable by the processor system to determine a value of a variable related to a distribution of force on the rigid seat pan over time. The processor system may, for example, execute instructions stored on the memory system to provide information via the user interface system to a user of the wheelchair based upon the distribution of force on the rigid seat pan over time to assist the user to adjust a seating position of the user in accordance with parameters stored in the memory system. The user interface system comprises a display.

In a number of embodiments, the sensor system includes at least four force sensors. Regardless of the number thereof, the force sensors may, for example, include strain gauges. In a number of embodiments, each of the force sensors measures tensile and compressive force.

The variable may, for example, be a center of pressure or force on the rigid seat pan. A neutral value or a neutral range of values for the variable may, for example, be correlated with a normal or neutral seating position. Predetermined values of the variable outside of the neutral range of values may, for example, be classified as types of pressure relief. Types of pressure relief may, for example, include a leftward pressure relief, a rightward pressure relief, a forward pressure relief and an upward pressure relief or lift. A total force on the rigid seat pan may also be measured or determined and used in determining at least one type of pressure relief.

In a number of embodiments, an effective pressure relief event is determined to have been achieved if a predetermined cumulative period of time passes that the value of the variable indicates one of the types of pressure relief is achieved (that is, if a predetermined cumulative period of time has passed wherein the value of the variable is indicative of the occurrence of the type of pressure relief). A counter or timer may, for example, be started when a value of the variable indicates one of the types of pressure relief has begun and wherein the counter is paused if the value of the variable no longer indicates that one of the types of pressure relief is occurring for a first predetermined period of time. The counter may, for example, be restarted if, within a second predetermined period of time, the value of the variable once again indicates that one of the types of pressure reliefs is occurring. The counter may, for example, be stopped and reset to zero if the value of the variable does not indicate that one of the types of pressure reliefs is occurring within the second period of time. Regardless of the methodology in determining if an effective pressure relief is achieved, a user may be notified via the user interface if the effective pressure relief event is achieved.

Changes in seating position may, for example, be classified as active or passive seating. Changes in seating position may, for example, be classified as active or passive seating based upon at least one machine learning methodology. In a number of embodiments, changes in seating position are classified as active or passive seating based upon at least one of a complex decision tree algorithm, a bagged decision tree algorithm, a fine KNN algorithm, and an SVM algorithm.

In a number of embodiments, changes in seating position are quantified by integrating deviations from the neutral seating position over time. Accumulated changes may be compared to a predetermined threshold value. In a number of embodiments, changes in seating position are traced for defined windows of time. A percentage of time of active seating may be determined for each of the defined windows of time.

In a number of embodiments, the wheelchair system includes a pedestal connected to the frame and a support structure connected to the pedestal. Each of the plurality of force sensors may be attached to the support structure. In a number of embodiments, the support structure includes four radially outward extending members and each one of the plurality (for example, four) of force sensors is attached to a different one of the radially outward extending members.

In a number of embodiments, each of the plurality of force sensors of the wheelchair systems hereof is independently connected to the frame.

In a number of embodiments, the memory system includes readable instructions that are executable by the processor system to provide user instructions to the user to adjust seating to perform pressure relief in accordance with parameters stored in the memory system. The user instructions comprise reminders to the user via the user interface system to adjust the seating position. The processor system may, for example, be configured to store data regarding at least one of the user instructions or a user action in the memory system. In a number of embodiments, the processor system monitors to determine if an effective pressure relief event has occurred. The user may, for example, be alerted via the user interface system when a predetermined event time period has elapsed after a previously determined effective pressure relief event. The user may be alerted via the user interface system by at least one of visible information, audible information, or tactile information (in general, sensory information). In a number of embodiments, the user is alerted via the user interface to increase magnitude of user movement, if necessary, to achieve an effective pressure relief event. In a number of embodiments, the user is informed of how to perform at least one of the types of pressure relief via the user interface system.

The wheelchair system may further include a communication system in operative connection with the processor system. Data may be transmitted to a remote system via the communication system and/or data may be received from the remote system.

In a number of embodiments, the sensor system further includes at least one of a sensor to determine the location of the wheelchair, a sensor to determine the condition of the environment of the wheelchair, or a sensor to determine a variable related to the activity in which the user is involved. One or more of the instructions provided to the user may, for example, be dependent, at least in part, upon at least one of a location of the wheelchair, a condition of the environment of the wheelchair, or an activity in which the user is involved. One or more of the parameters may, for example, be dependent upon at least one of a location of the wheelchair, a condition of the environment of the wheelchair, or an activity in which the user is involved.

In embodiments wherein the wheelchair system includes a communication system in operative connection with the processor system, at least one processor of the processor system, at least one memory component of the memory system, at least one communication component of the communication system or at least one interface component of the interface system may, for example, be provided by a personal communication device. The personal communication device may, for example, be a smartphone or a tablet computer.

A personal communication system interface may, for example, be operatively connected to the wheelchair and include a connector adapted to be placed in operative or communicative connection with a cooperating connector of the personal communication device. In a number of embodiments, the connector provides operative or communicative connection between the sensor system and the personal communication device. The personal communication system may, for example, be placed in communicative connection with the wheelchair in a wired or wireless manner (for example, via BLUETOOTH and/or other protocol).

At least one application may, for example, be stored on the at least one memory component of the personal communication device. The application may be executed by the at least one processor of the personal communication device. The at least one application is adapted to request data from the sensor system and runs as a background service on the personal communication device. In a number of embodiments, the at least one application is adapted to sense when the personal communication system is in communication with the sensor system and to automatically request data from the sensor system when the personal communication system is in communication with the sensor system. In a number of embodiments, the at least one application requests data periodically from the sensor system as long as the sensor system is in communication with the personal communications device.

In a number of embodiments of wheelchair systems hereof, the wheelchair is a manually powered wheelchair. The wheelchair may, alternatively be a powered wheelchair or a power assisted wheelchair.

In a number of embodiments, the processor system provides information via the user interface system to a user of the wheelchair based upon the distribution of force on the rigid seat pan over time regarding seating posture. Instructions may, for example, be provided to the user to assist the user to adjust the seating posture of the user in accordance with parameters stored in the memory system.

In another aspect, a method of tracking seating activity of a user in a wheelchair system (which includes a wheelchair including a frame, a plurality of wheels attached to the frame and a rigid seat pan includes providing a sensor system comprising a plurality of force sensors, the plurality of force sensors including at least three force sensors, each of the plurality of force sensors being attached to the frame and being positioned at a different position (relative to the frame), the rigid seat pan being connected to or placed in (operative) contact with each the plurality of force sensors at a different position on the rigid seat pan so that the rigid seat pan does not contact the frame and forces on the rigid seat pan are transferred to the plurality of force sensors) includes providing a processor system, each of the plurality of force sensors being in communicative connection with the processor system, providing a memory system in communicative connection with the processor system, and executing instructions stored on the memory system via the processor system to determine a value of a variable related to a distribution of force on the rigid seat pan over time. Embodiments of the method may further be characterized as described above and elsewhere herein.

In a further aspect, a method of providing information regarding seating activity to a user of a wheelchair (which includes a frame, a plurality of wheels attached to the frame and a rigid seat pan, includes providing a sensor system comprising a plurality of force sensors, the plurality of force sensors comprising at least three force sensors, each of the plurality of force sensors being attached to the frame and being positioned at a different position (relative to the frame), the rigid seat pan being connected to or placed in (operative) contact with each the plurality of force sensors at a different position on the rigid seat pan so that the rigid seat pan does not contact the frame and forces on the rigid seat pan are transferred to the plurality of force sensors) includes providing a processor system, each of the plurality of force sensors being in communicative connection with the processor system, providing a memory system in communicative connection with the processor system; providing a user interface system in communicative connection with the processor system, executing instructions stored on the memory system via the processor system to determine a value of a variable related to a distribution of force on the rigid seat pan over time, and providing information via the user interface system to a user of the wheelchair based upon the distribution of force on the rigid seat pan over time to assist the user to adjust a seating position of the user in accordance with parameters stored in the memory system. Embodiments of the method may further be characterized as described above and elsewhere herein.

In still a further aspect, a method of tracking seating activity of a user in a wheelchair system (which includes a wheelchair having a frame, a plurality of wheels attached to the frame and a rigid seat pan) includes measuring a distribution of force on the rigid seat pan over time and executing instructions stored on a memory system via a processor system to determine a value of a variable related to the distribution of force on the rigid seat pan over time. Embodiments of the method may further be characterized as described above and elsewhere herein.

In a number of embodiments of systems, devices and method hereof, data may be collected and processed from individual force sensor/load cells and other sensors. Algorithms (including, for example, artificial intelligence (AI) and machine learning) may, for example, be used to process sensor data into sitting position, propulsion technique, safety, and total weight. Algorithms may also be used to identify whether sitting positions constitute pressure relief based on default values or individual clinician guidance. Various state indices may be used to track different types of pressure relief, propulsion technique, safety related actions, and weight management, and a determination can be made of when clinician guidance is being met. The systems, devices and methods hereof provide the ability to display real-time guidance on pressure relief, propulsion technique, safety related actions, and weight management to users and clinicians, and to store the data to track progress. Based on collected data, systems, devices and/or methods hereof may, for example, determine whether smaller movements in sitting positions constitute active sitting that may lessen the need for traditional pressure relief maneuvers. Systems, devices and/or methods hereof may further determine wheelchair propulsion patterns and track other types of wheelchair activity. Algorithms may be provided to make a system hereof contextually aware. Contextual awareness may, for example, be used so that pressure relief instructions are not given in scenarios when a user has determined he or she does not wish to be so instructed. In general, systems, devices and/or methods hereof promote positive health behaviors (that is, safety and weight maintenance).

The present devices, systems, and methods, along with the attributes and attendant advantages thereof, will best be appreciated and understood in view of the following detailed description taken in conjunction with the accompanying drawings.

BRIEF DESCRIPTION OF THE DRAWINGS

FIG. 2A illustrates a top perspective view of a portion of a wheelchair frame hereof with the seat disassembled therefrom.

FIG. 2B illustrates a side view of the portion of the wheelchair frame of FIG. 2A.

FIG. 2C illustrates a front view of the portion of the wheelchair frame of FIG. 2A.

FIG. 10B illustrates a table setting forth data on clinician and machine learning algorithm classification of manual wheelchair users as exhibiting passive seating, active seating or a degree of active seating.

FIG. 11A illustrates a perspective view of a frame of a foldable manual wheelchair in a folded state with the seat removed, which includes a force sensor array hereof.

FIG. 11B illustrates a perspective view of the frame of FIG. 12A in an extended state.

FIG. 11C illustrates a top perspective view of the frame of FIG. 11A in an extended state with the seat removed.

FIG. 11D illustrates a side view of the frame of FIG. 11A in an extended state.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a sensor" includes a plurality of such sensors and equivalents thereof known to those skilled in the art, and so forth, and reference to "the sensor" is a reference to one or more such sensors and equivalents thereof known to those skilled in the art, and so forth. Recitation of ranges of values herein are merely intended to serve as a shorthand method of referring individually to each separate value falling within the range. Unless otherwise indicated herein, and each separate value as well as intermediate ranges are incorporated into the specification as if it were individually recited herein. All methods described herein can be performed in any suitable order unless otherwise indicated herein or otherwise clearly contraindicated by the text.

Figure 6A:
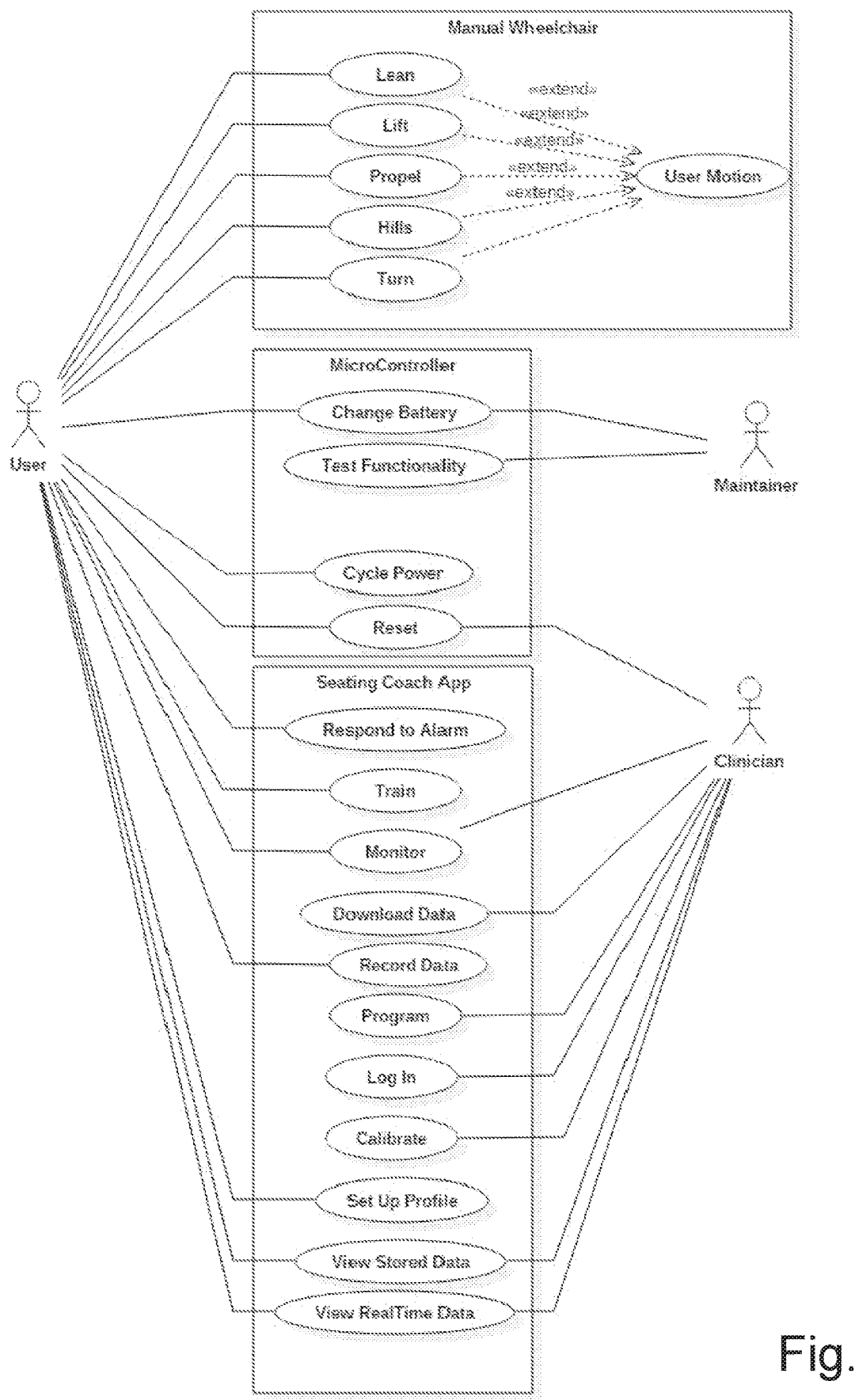
FIG. 6A illustrated an embodiment of a use case diagram for a system hereof.
Figure 6B:
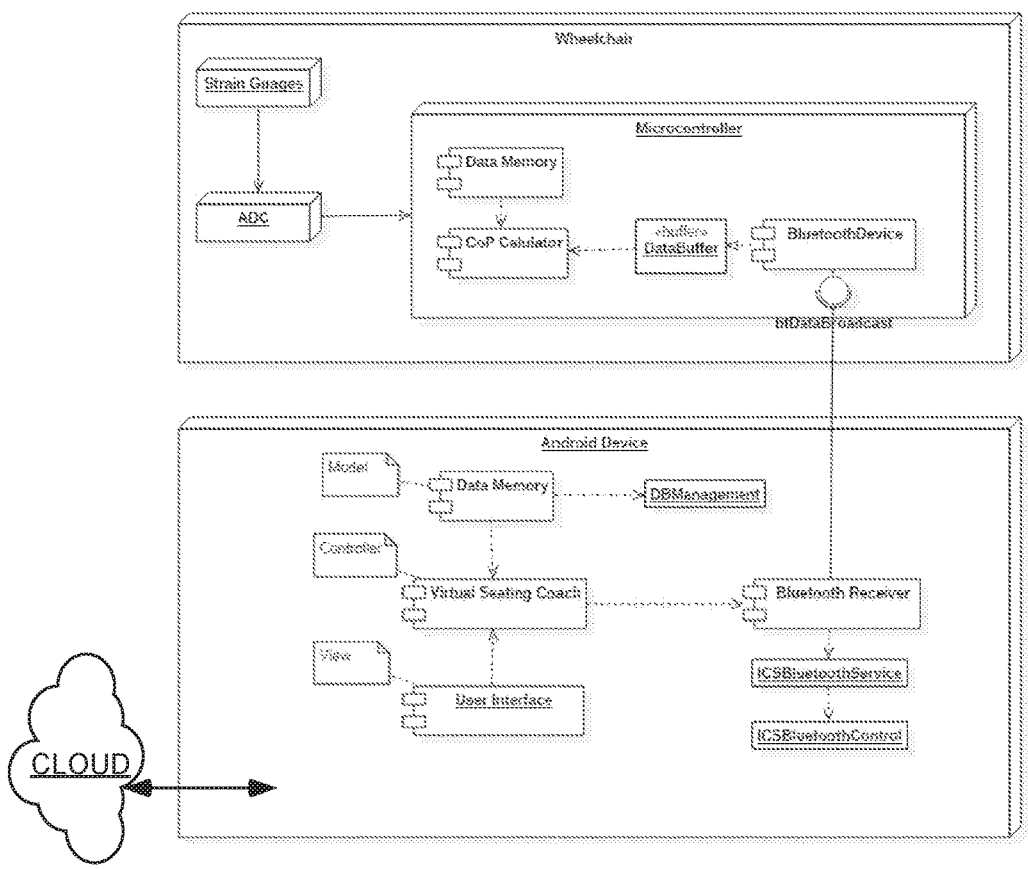
FIG. 6B illustrated schematically an embodiment of data processing in onboard electronic circuitry of a wheelchair and personal communication devices, as well as data communication therebetween.

In general, in the systems hereof, the wheelchair seat pan is supported on a structure including an array of or a plurality of force sensors or load cells (for example, strain gauges or other suitable sensors) from which the user's weight/body mass, center of force/pressure, seating position and seating activity (for example, motion within the seat) may be determined. The force sensors or load-cells are operationally coupled to, for example, electronic circuitry of the wheelchair including, for example, a microprocessor or microcontroller, which stores and processes data locally and/or uploads the data to a personal communication device or other local smart device for further processing and display. The personal communication device may, for example, be used to send the data to the cloud and/or other remote system for collection or further processing as illustrated in FIG. 6B. Sensors may also, for example, be located in one or more footrests of the wheelchair to better discriminate different sifting postures and record the total weight of the user. In a number of representative embodiments, the systems hereof are described for use in connection with manual wheelchairs. However, the systems hereof may, for example, be used in connection with any wheelchair (including powered wheelchairs) via which a distribution of force or center of force/pressure upon the seat may be determined. Such wheelchairs may, for example, include a rigid seat/seat pan.

The practical wheelchair virtual seating coach systems, devices and methods hereof support community integration by traveling with the wheelchair user and promoting the participation in many activities of daily living through promotion of active seating and pressure relief. Sensors, machine learning, and regular feedback with positive reinforcement are used to determine, for example, when a person is actively sifting in their wheelchair and/or performing regular pressure relief versus sifting passively or statically. Promotion of active sifting and/or performance of pressure relief will reduce pressure ulcers among the manual wheelchair users.

The systems, devices and methods hereof provide intelligent information, including, for example, instructions or reminders, to wheelchair users to change their seated posture or to perform pressure relief. The systems, device and methods hereof address behavioral, environmental and equipment complications that play a significant role in the progressive inactivity, frustration and injury often experienced by wheelchair users. Systems, devices and methods hereof thus provide greater control of the health of the user's seated tissue and greater freedom to participate in the community at large, improving the user's quality of life.

Wheelchair users and their clinicians indicate that they are unsatisfied with current technology and are concerned that a wheelchairs users' lifestyles are impaired by the lack of appropriate technology or that it will be negatively affected in the future as the users age. The ability to perform sitting postural changes and conduct pressure relief is a substantial indicator of one's ability to live at home and to participate in one's community, particularly when using a manual wheelchair. Technology, such as the present systems, devices and methods, to assist with mobility and seating are among the most important tools that clinicians can provide to manual and/or powered wheelchair users to promote independence, community participation, and quality of life.

With respect to systems, devices and methods hereof, the terms "electronic circuitry", "circuitry" or "circuit," as used herein include, but is not limited to, hardware, firmware, software or combinations of each to perform a function(s) or an action(s). For example, based on a desired feature or need. a circuit may include a software controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "software," as used herein includes, but is not limited to, one or more computer readable and/or executable instructions that cause a computer or other electronic device to perform functions, actions, or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

In a number of representative embodiments, data is processed, and information is provided to, for example, a manual wheelchair user (and/or communicated to one or more remote systems and/or the cloud), at least in part, via a personal communication device. However such functions may be carried out (in whole or in part) via other processor systems, which may be in operative connection with, embedded within, or integrated with a wheelchair or remote from the wheelchair. For example, a communication system may be integrated or operatively connected with the wheelchair. Likewise, functionality, including processing, may be distributed between systems integrated with wheelchair and, for example, another system such as a personal communication device and/or a remote system which may be placed in operative/communicative connection with the wheelchair. The use of personal communication devices may, for example, provide one manner of retrofitting existing wheelchairs to provide systems, devices and methods hereof.

As used herein, the term "personal communications device" refers to a portable or mobile device which includes a communication system, a processor system, a user interface system (for example, a visual feedback system including a touchscreen or other display, an auditory feedback system, and a tactile feedback system, an user input system etc.) and an operating system capable of running general-purpose applications. Examples of personal communications devices include, but are not limited to, smartphones, tablet computer and custom devices. As used herein, the term "tablet computer" or tablet, refers to a mobile computer with a communication system, a processor system, at least one user interface as described above (typically including a touchscreen display), and an operating system capable of running general-purpose applications in a single unit. As used herein, the term "smartphone" refers to a cellular telephone including a processor system, at least one user interface as described above (typically including a touchscreen display), and an operating system capable of running general-purpose applications. Such personal communication devices are typically powered by rechargeable batteries and are housed as a single, mobile unit. Moreover, in a number of embodiments personal communications devices are able accept input directly into a touchscreen (as opposed to requiring a keyboard and/or a mouse). Personal communications devices as typically provide for internet access through cellular networks and/or wireless internet access points connected to routers. A number of representative embodiments of systems and/or methods hereof are discussed in connection with the user of a smartphone as the personal communication device.

Figure 1A:
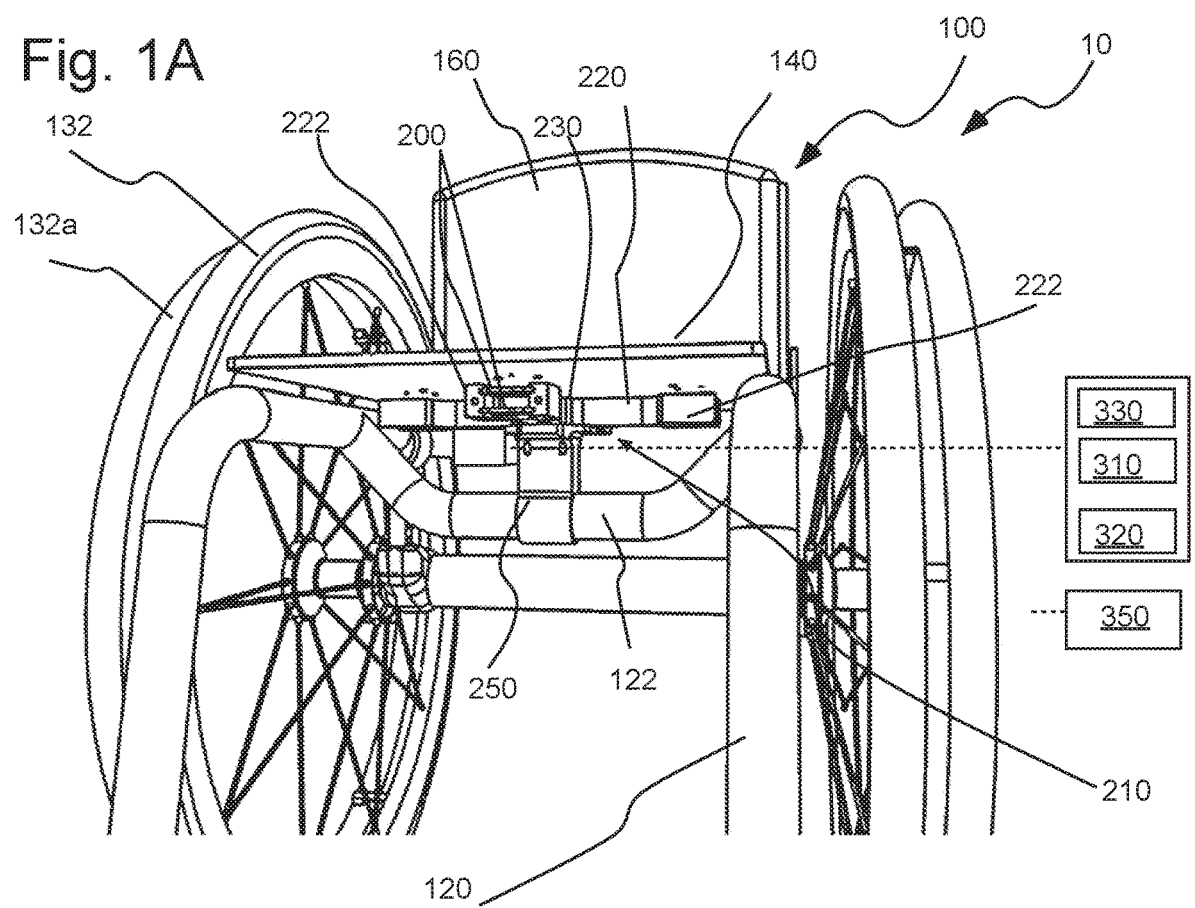
FIG. 1A illustrates a front perspective view of embodiment of a manual wheelchair hereof.
Figure 1B:
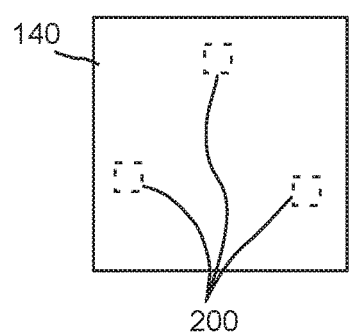
FIG. 1B illustrates schematically a top plane view of a rigid, weight-bearing member such as a seat pan or footrest of a wheelchair system hereof in operative connection with a sensor system including three force sensors positioned at three different or unique positions in contact with the lower surface of the rigid seat pan.
Figure 1C:
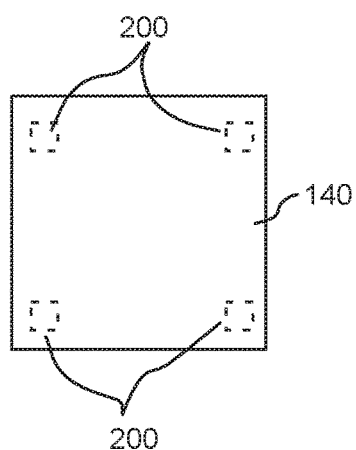
FIG. 1C schematically illustrates a rigid weight-bearing member of a wheelchair system hereof in operative connection with a sensor system including four force sensors positioned in a first pattern at four different or unique positions in contact with the lower surface of the rigid seat pan.
Figure 1D:
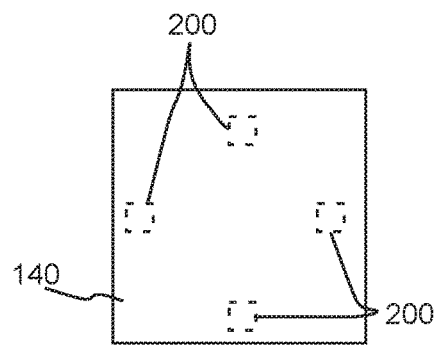
FIG. 1D illustrates schematically a rigid weight-bearing member of a wheelchair system hereof in operative connection with a sensor system including four force sensors positioned in a second pattern at four different or unique positions in contact with the lower surface of the rigid seat pan.

FIG. 1A illustrates a manual wheelchair system 10 hereof. Wheelchair system 10 includes a wheelchair 100 including a frame 120 and a plurality of wheels (including rear wheels 132, which are manually powered by a user via hand rails 132a, and front caster wheels—not shown) attached to frame 120. Wheelchair 100 further includes a rigid seat pan 140, a foot rest 144 (see, FIG. 2B) and a seat back 160. As used herein with respect to rigid seat pan 140 and other rigid seat pans hereof, the term "rigid" refers to a seat pan formed of a material which does not deform to any significant extent during normal use of wheelchair 100 by a user thereof. In a number of representative embodiments, a rigid seat pan hereof does not deform by more than 0.1 inches or 0.05 inches while supporting the mass of the user during use of the wheelchair. In general, a seat pan for use herein should be sufficiently rigid to be modeled as a rigid member in, for example, determining a value of a variable indicative of the distribution of force on rigid seat pan with sufficient accuracy to determine user movement and/or position as described herein.

A sensor system hereof may, for example, include a plurality of force sensors that are placed in operative connection with a bottom surface of rigid, weight-bearing member such as seat pan 140 or foot rest 144 (see, for example, FIG. 2A). Each of the plurality of force sensors is positioned at a different, unique position with respect to frame 120 and to rigid seat pan 140. In general, at least three force sensors are provided in a nonlinear arrangement to define a measurement or sensor array plane. In a number of embodiments, at least four force sensors, each having a different, nonlinear unique position are provided to form a generally planar sensor array. Each of the four sensors may, for example, be positioned in a different quadrant of a rigid member such as seat pan 140. In the illustrated embodiment of FIGS. 1A through 4, four force sensors 200 are illustrated. Rigid seat pan 140 is connected to each the plurality of sensors 200 at different positions on rigid seat pan 140 so that the rigid seat pan 180 does not contact frame 120. The sensor array including sensors 200 interconnects with seat pan 140 and supports the weight of seat pan 140 and any user thereon. Pressure/forces on seat pan 140 are transferred to the sensor array. In number of embodiments, each of forces sensors 200 include at least one strain gauge.

In a number of studied embodiments, rigid seat pan 140 was formed form carbon fiber. Such a carbon fiber seat pan 140 is lightweight and stiff/rigid, allowing portions of it to be cantilevered via sensors 200 as described herein. Rigid seat pan 140 is suitably rigid to be modeled mathematically as a rigid member in, for example, determining a value of a variable indicative of the distribution of force on rigid seat pan 140.

In a number of embodiments, sensors 200 measures compressive force (oriented downward with respect to the orientation of the wheelchair during normal use and with respect to gravity). In a number of embodiments, sensors 200 measure both compressive force and tensile force (oriented upward with respect to the orientation of the wheelchair during normal use and with respect to gravity). In that regard, depending upon a center of pressure/force on a rigid, weight-bearing member, and the position of sensors 200, some sensors may be in compression while other sensors are in tension.

Each of the plurality of force sensors 200 is in communicative connection with a processor system 310 (illustrated schematically in FIG. 1A). Processor system 310 comprises one or more processors such as microprocessors. A memory system 320 is in operative connection with processor system 310. A user interface system 330 is also in operative connection with processor system 310. Readable instructions (software components) are stored on memory system 320 and are executable by processor system 310. In a number of embodiments, such readable instructions are executable to determine a value of a variable related a distribution of force on the rigid seat pan 140.

The processor system 310 may, for example, provide information (for example, instructions) via the user interface system 330 to the user of wheelchair 100 based upon the value of the variable related to the distribution of force (or pressure) on rigid seat pan 140 to assist the user to adjust a seating position of the user in accordance with parameters stored in memory system 320. In a number of embodiments, hereof the variable is a center of force/pressure on rigid seat pan 140. The distribution of force or pressure over time may be related to, for example, seating position (including seating posture) to provide instructions regarding pressure relief and/or posture improvement. Pressure relief is, for example, effected by period movement in seating position. Poor seating posture may for example, be associated with a tendency to lean one way or another, which may be associated with non-centered force/pressure distribution.

Figure 3:
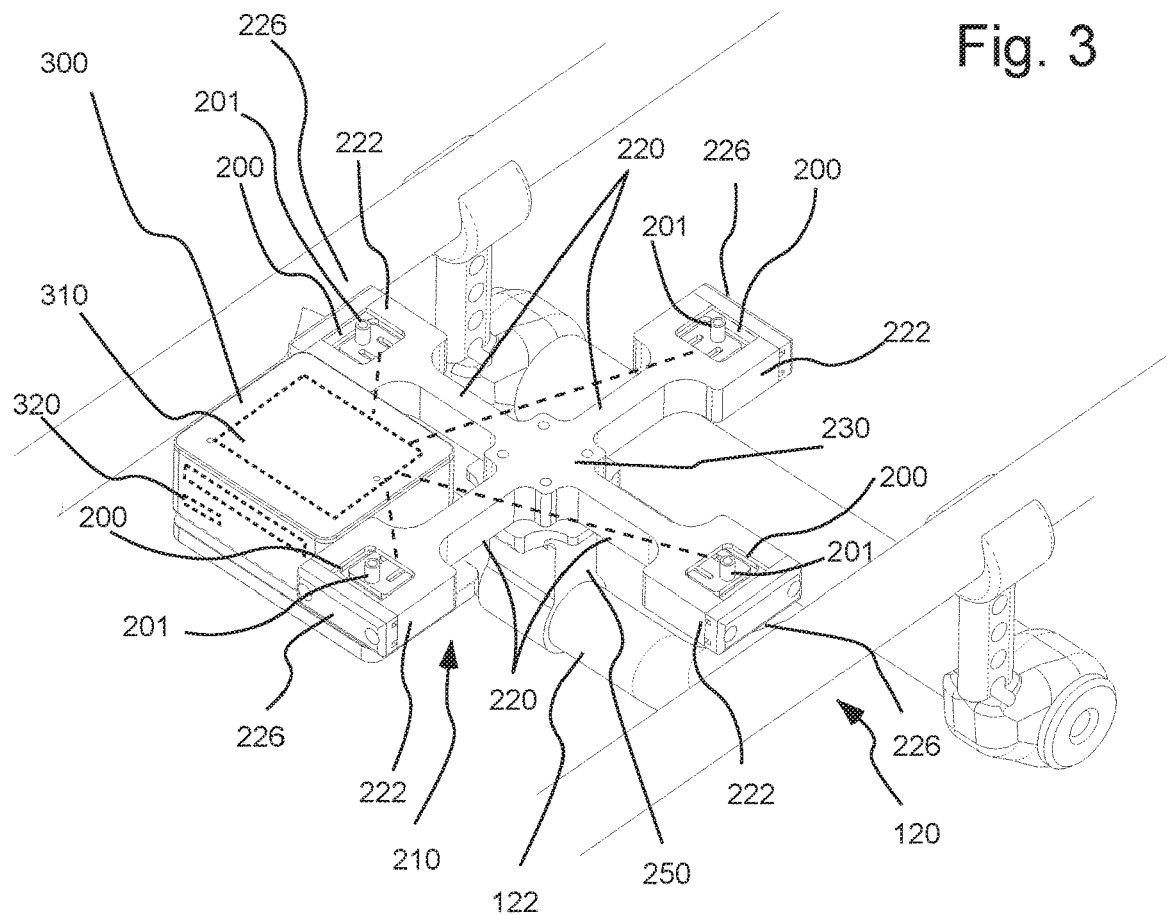
FIG. 3 illustrates a top perspective view of a pedestal and sensor support assembly of the wheelchair of FIG. 2A.
Figure 4:
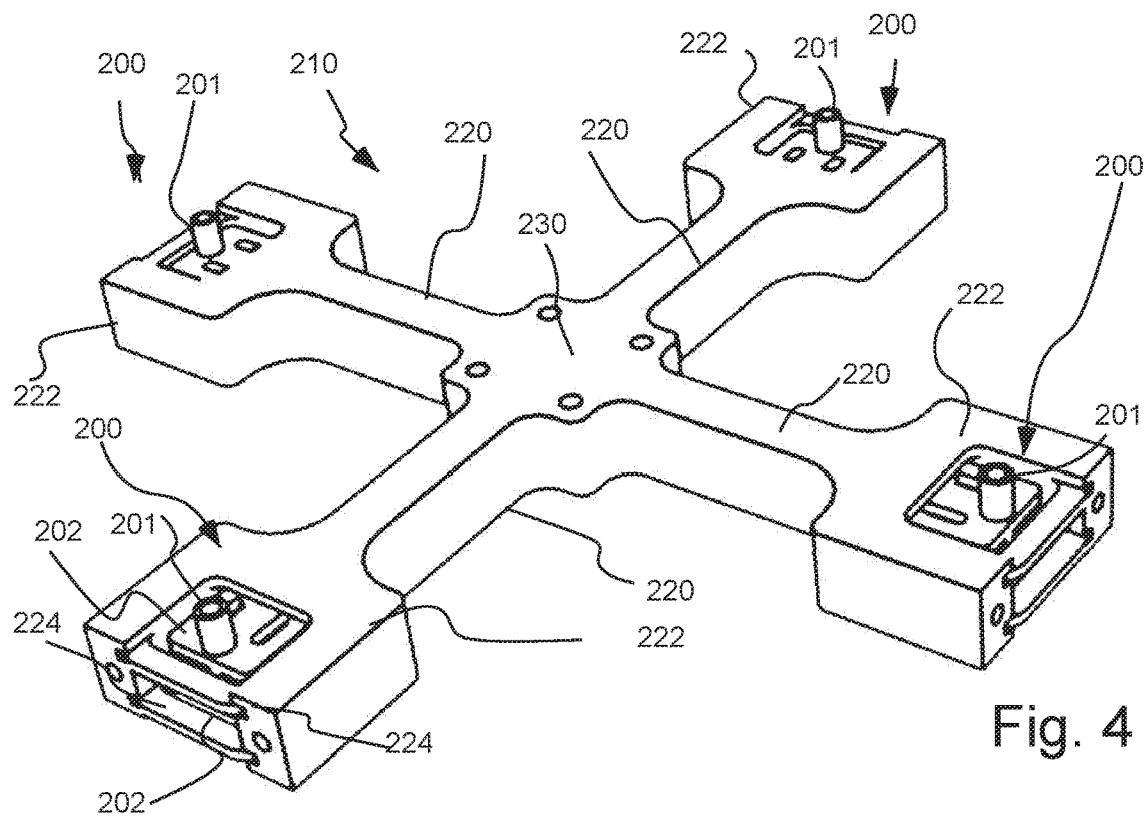
FIG. 4 illustrates a perspective view of the sensor support of the wheelchair of FIG. 2A.

In the embodiment of FIGS. 1A through 4, each of force sensors 200 is supported upon a support member 210. An electronic circuitry housing 300 may, for example, be attached to support member 210 and house electronic circuitry in communicative connection with sensors 200. In a number of studied embodiments, support member 210 was formed of machined aluminum. With reference, for example, to FIGS. 3 and 4, in the illustrated embodiment, support member 210 comprises four extending members 220, which extend outwardly or radially and generally horizontally outwardly from a center section 230. Each extending member 220 includes a seating member 222 at a distal end thereof in which sensors 200 are seated. A connector 201 may extend from each sensor 200. Connectors 201 may, for example, form an interconnection with a cooperating connector (not shown) extending from a lower surface of seat pan 140. In the illustrated embodiment, extending members 220 extend from center section 230 at generally right angles to adjacent extending members 220 in the formation of a cross (or intersecting perpendicular lines). With reference to, for example, FIG. 3, center section 230 is attached via connectors such as screws, bolts and/or other connectors/fasteners as known in the art to a pedestal 250 which is attached to frame 120. In the illustrated embodiment, pedestal 250 is connected to a cross member 122 of frame 120 and extends generally vertically therefrom to form a connection with support member 210.

In a number of studied embodiments, each of force sensors 200 included two 1000Ω strain gauge sensors 202 (see, for example, FIG. 4) applied in a half-bridge configuration, allowing for bi-directional (compression and tension) detection of forces. As described above, in the case of the embodiment of FIGS. 1A through 4, sensors 200 are arranged at four points on rigid seat pan 140 to detect forces in the vertical direction (that is, generally parallel to the orientation of gravity when wheelchair 100 is resting on a flat, horizontal surface), allowing for the calculation of a value of a variable indicative of distribution of force on rigid seat pan 140 in both the lateral and the fore/aft directions. Additionally, dynamic forces acting upon the seat in bouts of activity (e.g. wheel propulsion, pressure relieving exercises, etc.) can also be detected.

As illustrated, for example, in FIG. 4 each end or seating member 220 includes two grooves or seatings 224. Each groove 224 seats one of sensors 202. As, for example, illustrated in FIG. 3, an end cap 226 on each end or seating member 222 of extending members or legs 220 holds sensors 202 in place. Grooves 224 are dimensioned to allow the sensors 202 to float laterally over a small distance, which assists in preventing the introduction of bending caused by internal loading arising from any small misalignment in the final assembly. The half-bridge force sensors 202 used in a number of embodiments were OEM components which may, for example, be used in the bathroom scale industry and are available in bulk for approximately $0.40 per sensor. Sensors 202 include a stamped metal tab with a two-resistor strain gage bonded to thereto and leads soldered to the gage. An additional layer of RTV silicone (room-temperature-vulcanizing silicone) covers the gage, providing protection for the gage and strain relief for the leads. The design illustrated in, for example, FIG. 4 stacks two force sensors 202 back-to-back on each extending member or leg 220 of support 210, coupled with hardware, and fixed to rigid seat pan 140. Sensors 202 on each extending member or leg 220 are wired to form a full strain gage bridge, which mechanically amplifies the signal and, helps reject signal disturbances caused, for example, by temperature fluctuation and EMF. In other embodiments, a high-end two-resistor strain gages was used. However, such a two-resistor strain gage costs around $12 for each gage and requires significant labor time to apply and solder.

In a number of embodiments, the electronics within housing 300 were based on instrumentation amplifiers interfaced to a microprocessor board. Custom printed circuit boards (PCBs) 310, as shown schematically in FIG. 3 within housing 300, for the collection, storage and transmission of force and/or other data were fabricated. PCBs 310 were also developed for the power supply, amplifier board, and for connecting with a TEXAS INSTURMENTS® Wireless Sensor Tag board (available from Texas Instruments of Dallas, Tex.). A power supply 320 (illustrated schematically in FIG. 3) in the form of battery power (for example, a rechargeable battery or a non-rechargeable battery) was selected to supply power to the PCBs. Strain gauge validation was done for hysteresis/linearity. An inventory of sensors for a sensor system 350 (illustrated schematically in FIG. 1A) hereof in addition to force sensors 200 included, for example, light sensors, gyro sensors, accelerometers, temperature sensors etc. Firmware for the Wireless Sensor Tag was developed using the Texas Instruments TI-RTOS (a real-time operating system available from Texas Instruments) and BLE SDKs (BLUETOOTH lower energy software development kits available from Texas Instruments; BLUETOOTH is a wireless communications protocol managed by the Bluetooth Special Interest Group, headquartered in Kirkland, Wash.) to facilitate the collection and transmission of sensor data from the Sensor Tag and the amplifier board. TI-RTOS is a real-time operating system kernel used to handle precise scheduling of processes on-board the Sensor Tag. An application programming interface or API for interfacing the analog front-end integrated circuit chip (for example, the ADS130E08IPAGR, integrated circuit chip available from Texas Instruments) with the Sensor Tag via serial communication was also developed as part of the firmware.

Figure 5:
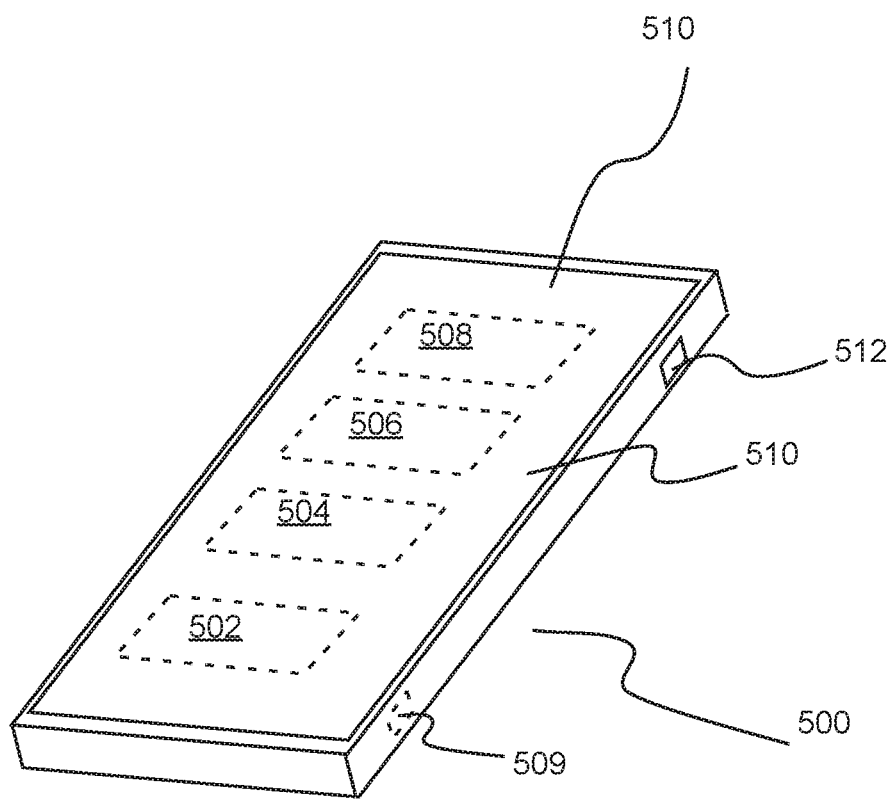
FIG. 5 illustrates schematically an embodiment of a personal communication device for use herein.

The circuit takes inputs from load sensors incorporated into the seating system, amplifies the signals and converts them for digital processing. In a studied embodiment, the amplifier board used four INA122 instrumentation amplifiers (available from Texas Instruments) and the ADS130E08 analog front-end described above, which includes a 12-bit analog-to-digital converter or ADC for converting the voltage data to a digital format. In a number of embodiments, a circuit using four Lithium-ion battery cells with a voltage regulator was designed, allowing for light-weight battery powering of the amplifier board. The analog front end or AFE on the amplifier board then uses the Sensor Tag to transmit the data in digital format via, for example, the BLUETOOTH protocol to, for example, a personal communication device such as a smartphone 500 (see FIGS. 2B and 5), which includes one or more applications for further processing. Schematics and printed circuit board (PCB) layout were completed using ALTIUM DESIGNER® (PCB design software available from Altium of La Jolla, Calif.) for both the amplifier board and the power supply board.

In another studied embodiment, a single board computer such as the UDOO® Neo (available from by Seco USA of Burlington, Mass.) was used in housing 300 to, for example, enable on board storage of load cell data during the trial, which can be subsequently processed to improve seated posture algorithms and to conduct post hoc analysis of unexpected results. The computer has sufficient computing power to offload substantial portions of the algorithm from the smartphone, which can improve smartphone battery life, and keep the operating system from stopping the Virtual Coach APP as a resource intensive process. In a number of embodiment using the UDOO Neo, five amplifier PCBs were used. The PCBs were tested to calibrate the no-load output voltage as 1.65V while supplying 3.3V. The gain resistors on the PCBs was calibrated using different weights from 1-50 lbs. ensuring that the dynamic range of the output voltages was within the 1.2V. Housing 300 was fabricated via 3D printing to hold the amplifier, battery, battery charging PCB, and the single board computer. A Kalman filter was used to remove low-frequency oscillation in the response from sensors 200.

Wheelchair 100 may, for example, include a holder or cradle 190 for smartphone 500 as illustrated in FIG. 2B. Holder 190 may further include communications ports to create a wired and/or wireless communicative connection between smartphone 500 and the electronic circuitry within housing 300. Such an "interfacing" or "docking" cradle is, for example, disclosed in US Patent Publication No. 2015/0209207, the disclosure of which is incorporated herein by reference. Digital data may be sent to smartphone 500 (for example, a smartphone using the ANDROID® operating system of Google, Inc. of Mountain View, Calif., which is available from virtually any wireless telephone provider) via a wired connection such as a USB cable or wirelessly as described above. For example, the BLUETOOTH or another wireless communications protocol can be used to provide communication between the system electronic circuitry and smartphone 500.

In a number of embodiments, the user interface system and a portion of the processor system of the wheelchair system 10 hereof is provided by a personal communication device such as smartphone 500. As known in the art and as illustrated schematically in FIG. 5, smartphone 500, includes a processor system 502, a memory system 504, a communication system 506 (which may, for example, include wireless cellular telephone connectivity (providing telephone and internet connectivity), radio-band or WiFi internet connectivity, BLUETOOTH wireless connectivity, infrared wireless connectivity, etc.) and an interface system 508 (including, for example, a touchscreen display 510, a microphone/speaker system 512, and a vibration mechanism). Smartphone 500 may also include a sensor system 509 including, for example, GPS, one or more accelerometers etc. Such sensors may be incorporated into or form a part of sensor system 350 of the systems, devices and methods hereof.

Figure 6C:
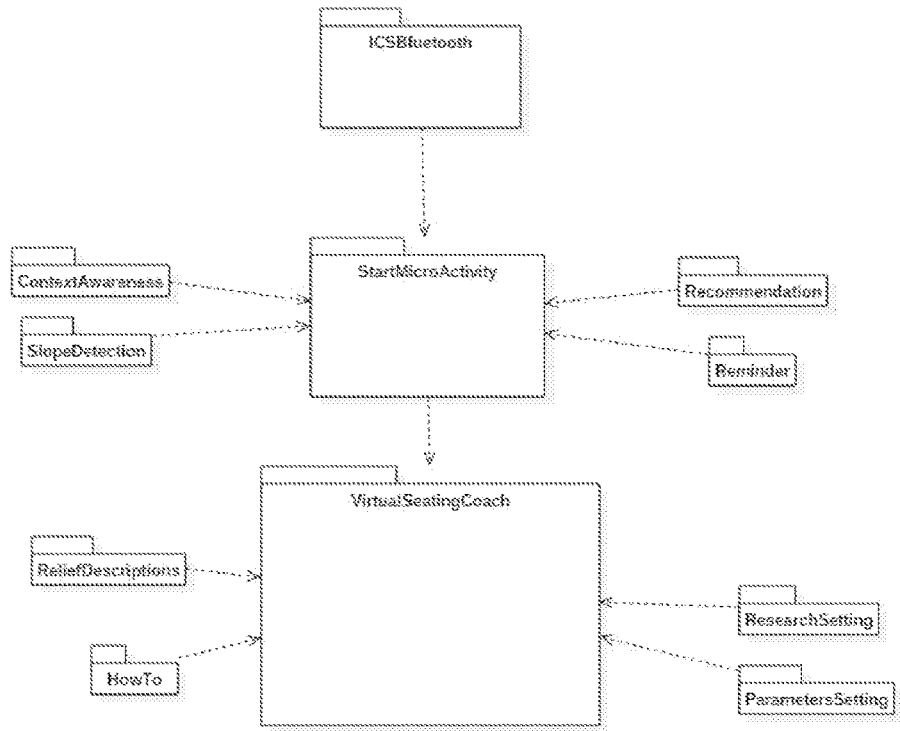
FIG. 6C illustrates schematically a high-level functional diagram of an embodiment a seating coaching application/methodology hereof.
Figure 6D:
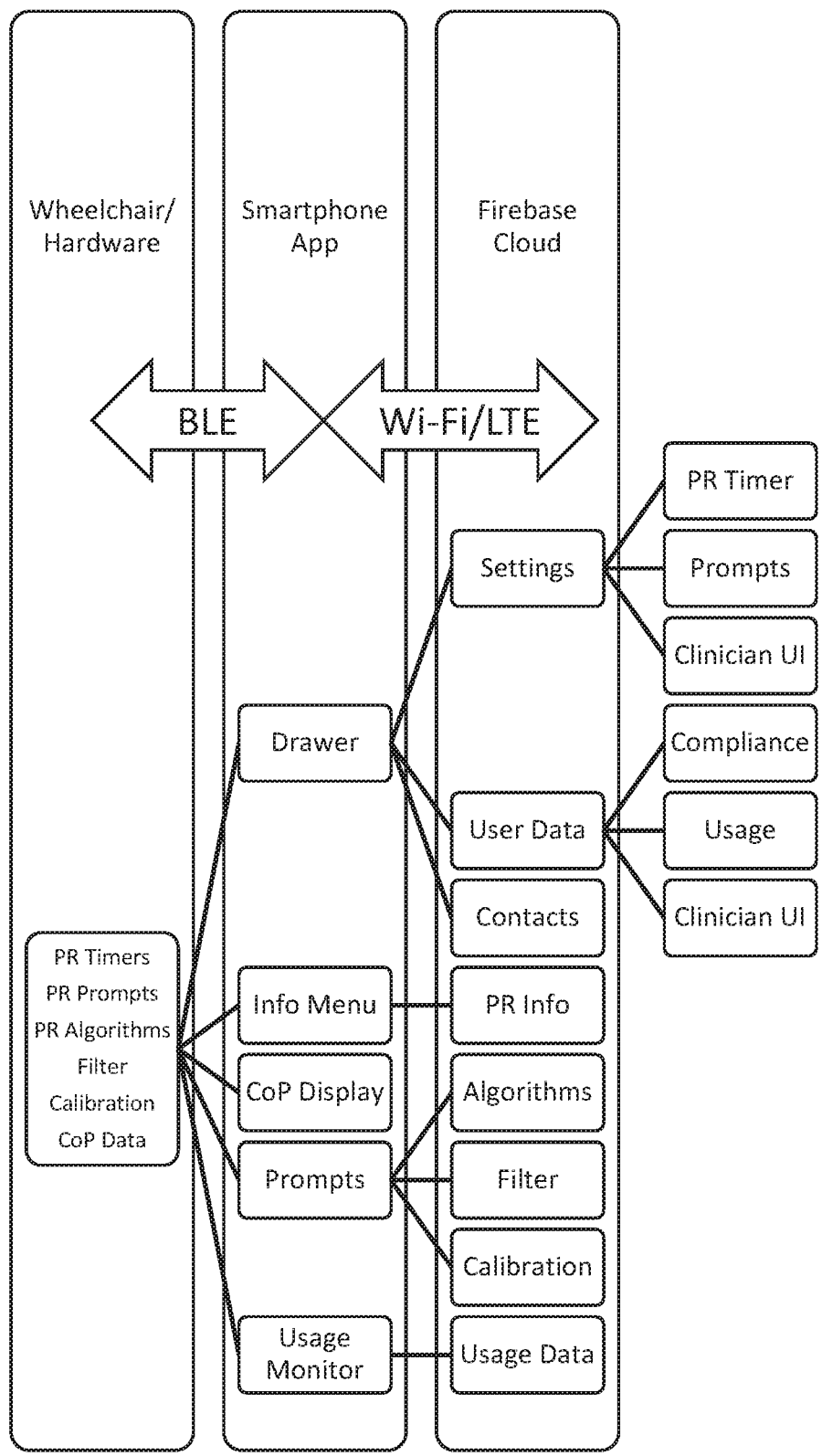
FIG. 6D illustrates schematically an embodiment of a communication scheme between wheelchair hardware via a smartphone app via BLUETOOTH Low Energy (BLE) and between the smartphone app and a remote/cloud-based FireBase database via a Wi-Fi and/or a cellular-based connection (for example, LTE, a 4G wireless communications standard).
Figure 6E:
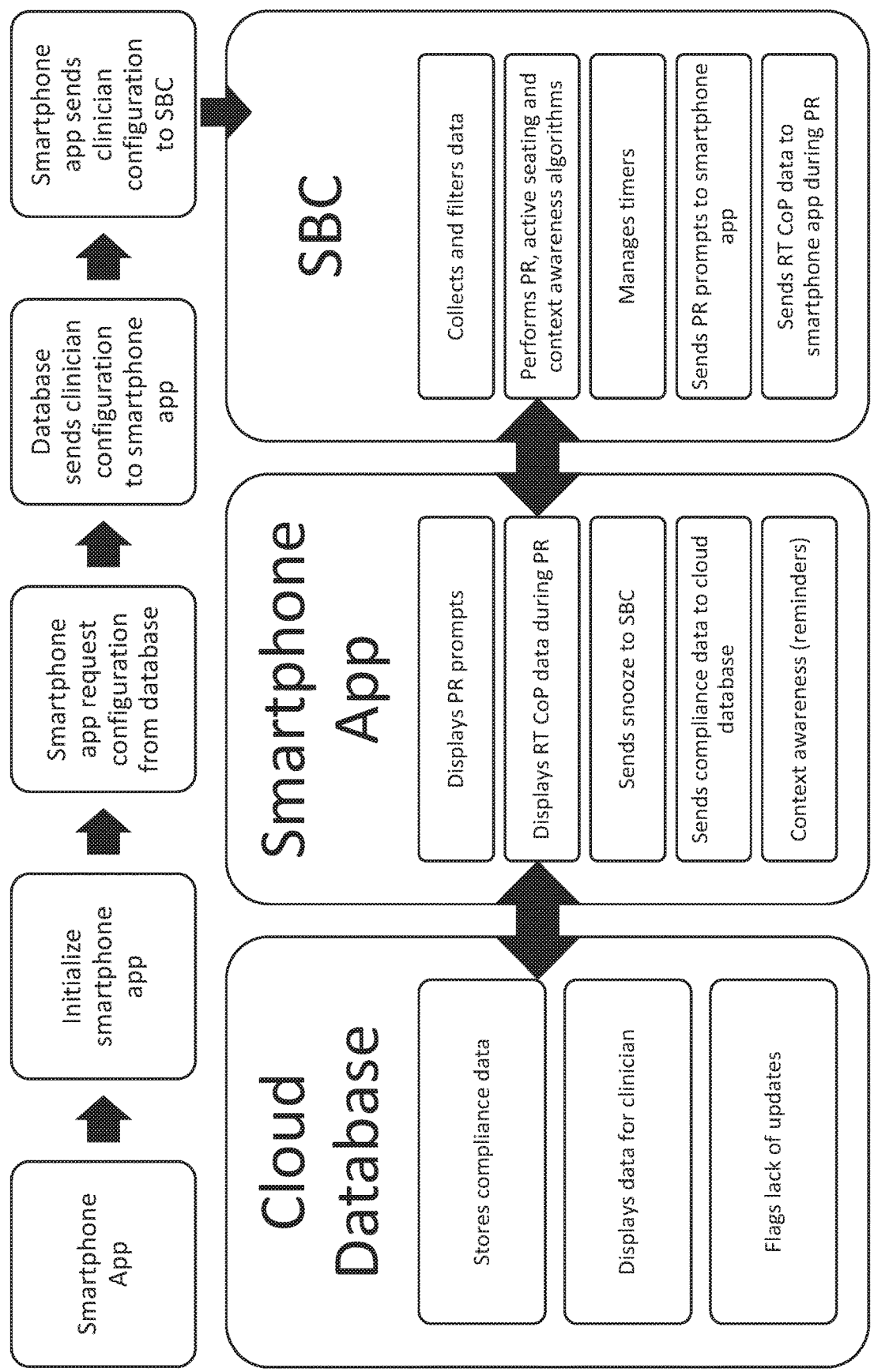
FIG. 6E illustrates an embodiment of a flow chart for remote, server-based computing.

A user interface application, along with sub-activities was created as an app or application for ANDROID smartphone 500. FIG. 6A illustrates an embodiment of a use case diagram for system 10. FIG. 6B illustrates schematically data processing in the electronic circuitry of wheelchair 100 and smartphone 500 and data communication therebetween. FIG. 6C illustrates schematically a high-level functional diagram of an embodiment a seating coaching application hereof. FIG. 6D illustrates schematically an embodiment of a communication scheme between wheelchair hardware via a smartphone app via BLUETOOTH Low Energy (BLE) and between the smartphone app and a remote/cloud-based FireBase database via a Wi-Fi and/or a cellular-based connection (for example, LTE, a 4G wireless communications standard). FIG. 6E illustrates an embodiment of a flow chart for remote, server-based computing.

In a number of studied embodiments, Firebase Real-time Database (a cloud-hosted database available from Google LLC of Mountainview, Calif.) and Crashlytics (a reporting solution for real-time analytics available from Crashlytics of Boston, Mass.) were used for the app, in combination with the User sign-in mechanism. The smartphone app could thereby be remotely accessed, and changes could be made as necessary in reaction to bugs and push tested updates to a user remotely. Additionally, app usage data by user could be collected.

As described above, in a number of embodiments hereof, the variable related to distribution of force on rigid seat pan 140 is a center of pressure or CoP (or, equivalently, the center of force) on rigid seat pan 140. The center of pressure of the user may be tracked and pressure relief maneuvers (for example, leftward leans, rightward leans, and forward leans) may be classified. A center of pressure value provides a single value magnitude for the degree of lean that can be used for monitoring pressure relief behavior, for providing feedback to the user, or (via predetermined thresholds), for identifying when an effective pressure relief event has been achieved/performed.

As part of a larger protocol, 40 manual wheelchair users were asked to perform pressure relief maneuvers, including leftward, rightward, and forward leans. In post processing of the data, raw strain measurements were converted to force using previously obtained calibration curves for each strain gauge. The force measurements were then converted to center of pressure in the horizontal (X) and vertical (Y) coordinates, according to the following equations:

$$CoP_X = \frac{-A*d}{A+C} + \frac{d}{2} \quad CoP_Y = \frac{-B*d}{B+D} + \frac{d}{2} + s$$

where A and C are forces on the left and right sides of the beam and B and D are forces on the back and front, respectively, d is the total length of the beam in each direction, and s is the offset between the center of the crossbeam and the center of the seat pan.

The center of pressure X and Y-coordinates were subsequently transformed into angle and magnitude values, according to the following equations:

$$\text{angle} = \tan^{-1}\left(\frac{CoP_Y}{CoP_X}\right) \quad \text{magnitude} = \sqrt{CoP_X^2 + CoP_Y^2}$$

A filter was then applied that set the angle value to zero when the magnitude was low. The filter threshold value was adjusted for each participant to eliminate the noise in the angle signal that came from electrical noise and small movements that did not represent intentional pressure relief maneuvers.

Figure 7A:
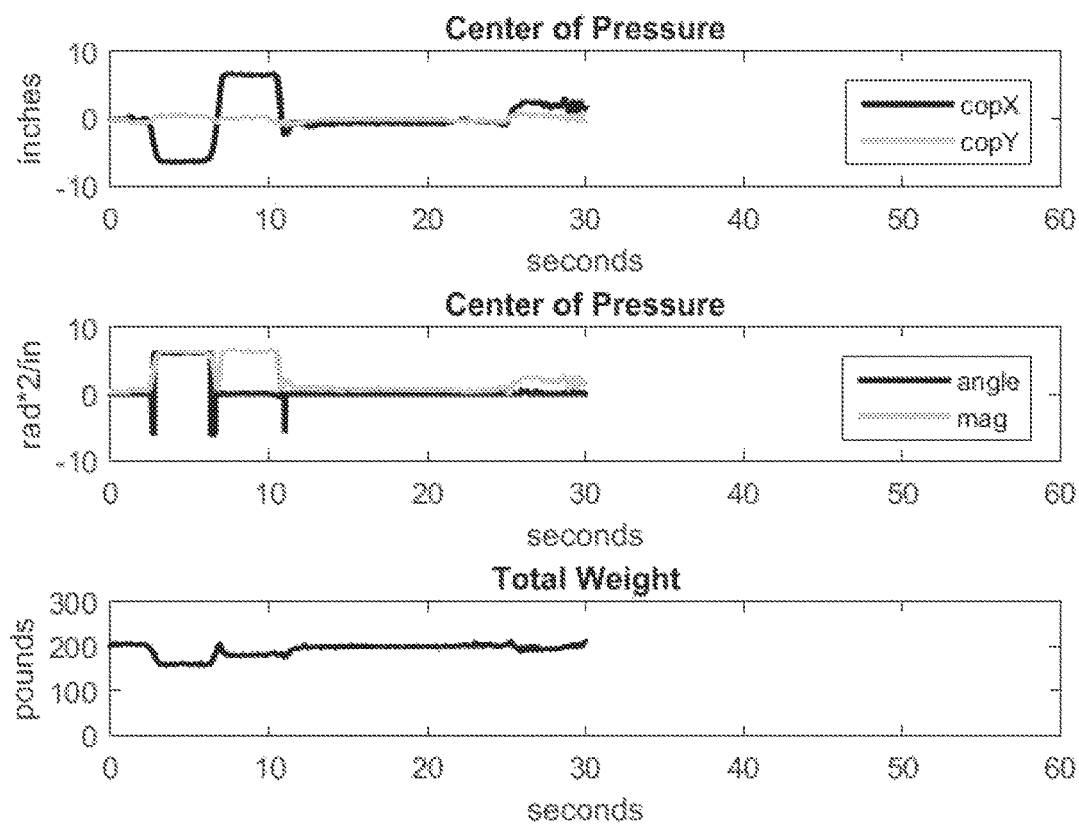
FIG. 7A illustrates graphs of center of pressure in the X and Y coordinates, angle and magnitude values, and total weight as the participant executed leftward and rightward leans

FIG. 7A shows graphs of center of pressure in the X and Y coordinates, angle and magnitude values, and total weight as the participant executed leftward and rightward leans. As would be expected, the x-coordinate of center of pressure (copX) moves significantly first in the negative, then the positive direction. The Y coordinate (copY) also moves in the positive direction, reflecting the fact that the participant is leaning forward while leaning leftward or rightward. The magnitude can be seen to increase substantially for both leftward and rightward leans with a leftward lean characterized by an angle value close to pi radians, and a rightward lean by an angle value close to 0 rad. Note that the scale for angle values is radians*2, so that the changes are clearly visible on the same set of axes used to display magnitude values.

Figure 7B:
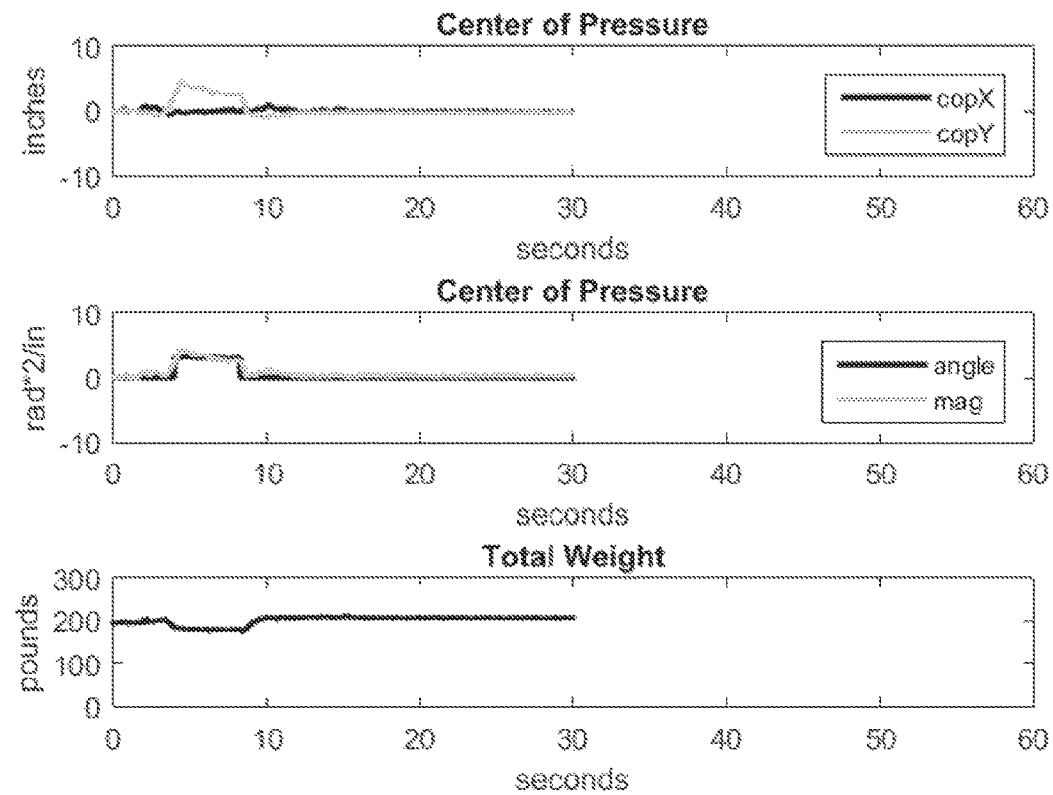
FIG. 7B illustrates graphs of center of pressure in the X and Y coordinates, angle and magnitude values, and total weight for a forward lean maneuver.

FIG. 7B shows the same set of graphs for a forward lean. The x-coordinate center of pressure can be seen to stay close to zero, while the Y coordinate moves substantially in the positive direction. Along with the increase in the magnitude value, the angle value is close to π/2 rad.

Figure 7C:
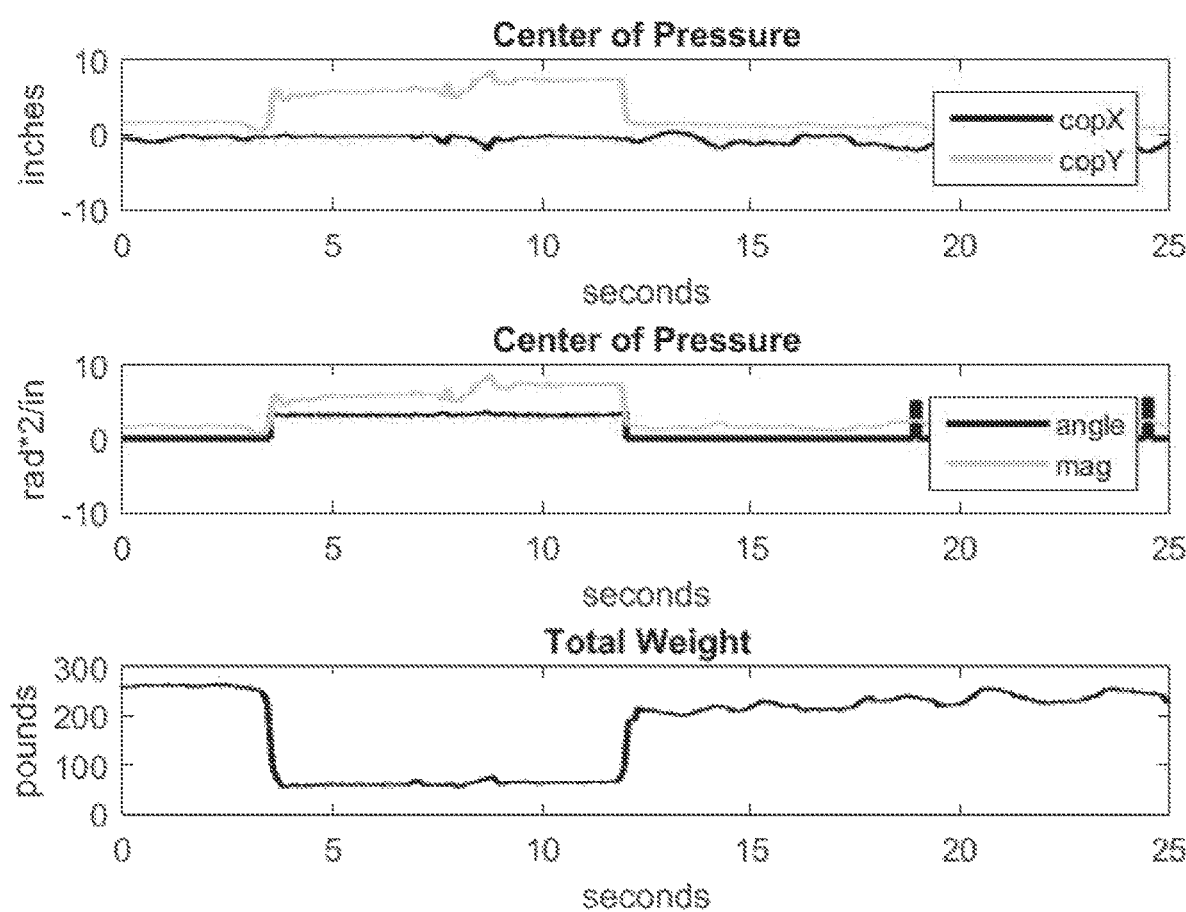
FIG. 7C illustrates graphs of center of pressure in the X and Y coordinates, angle and magnitude values, and total weight for a push-up, or lift off, pressure relief maneuver.

FIG. 7C shows the user doing a push-up, or lift off, pressure relief. As, in the current prototype set up, the center of the crossbeam is in front of the center of the seat pan, the center of pressure appears to move forward, when the user is not putting weight on the seat pan. FIG. 7C also shows that, unlike with a forward lean, the total measured weight on the seat pan decreases substantially for a push-up. Force/pressure on footrest 144 and/or the armrests of a wheelchair may also be monitored to characterize, for example, a push-up.

As can be seen in the data of FIGS. 7A through 7C, one can discriminate between leftward, rightward, and forward leaning pressure relief or PR maneuvers by observing the angular value of the user's center of pressure. However, since the angular value can vary continuously, thresholds may be determined to perform this classification or categorization. A representative approach is to divide the forward facing angular values into three sections—for example, 0≤π/3, π/3≤2 π/3, and 2 π/3≤π.

Alternatively, clinical expertise regarding proper pressure relief technique may dictate another division of angular values. For example, the acceptable angles for a forward lean may be a wider or narrower range then described above. Clinical expertise may also be important in establishing guidelines for what center of pressure magnitude values constitute effective PR; these values may or may not be different for different types of pressure relief.

While angle and magnitude values may be sufficient for differentiating between rightward, forward, and leftward leaning pressure relief maneuvers, the data demonstrate that they are insufficient to distinguish other types of typical pressure relief such as, for example, push-up/liftoff. A more complete understanding of users' sitting or seating behavior may thus be obtained by incorporating into the algorithm additional values, such as total force/weight.

Figure 8A:
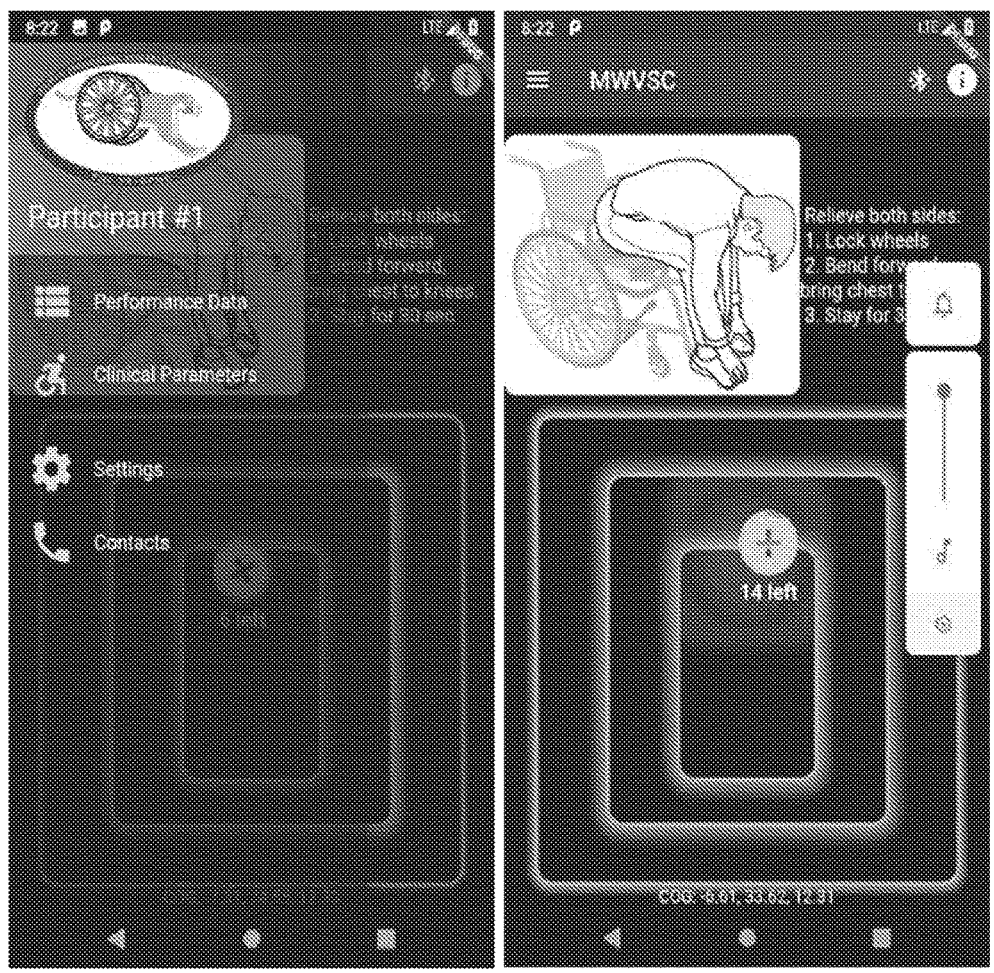
FIG. 8A illustrates embodiments of screen displays for a virtual seating coaching system, device or method hereof.
Figure 8B:
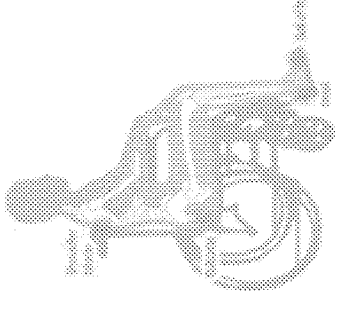
FIG. 8B illustrates embodiment of additional screen displays for a virtual seating coaching system hereof.

FIG. 8A illustrates embodiments of screen snapshots for display 510 which provide a reminder and instructions to a user to execute a forward lean pressure relief maneuver, provide feedback on associated center of pressure data, and provide information on the achievement of an effective pressure relief maneuver. In the illustrated embodiment, the pressure relief page on the right shows the relieving area and instructions of the relieving technique with a picture. A moving circle indicates the center of gravity on the seat which helps the user to shift weight correctly. A countdown timer under the circle may help the user know the remaining time left in this position. When sliding from the left side of the screen, there is an additional menu of reviewing performance data, changing clinical parameters and settings, and finding contact information. On the top of the screen, the BLUETOOTH icon shows the BLUETOOTH connection status. The information icon on the top right corner of the screen is linked to a help menu that contains information and articles about the importance of performing pressure relieving exercises as illustrated in FIG. 8B. Data related to notification and reminders may be uploaded to, for example, a Firebase database. Such data may, for example, show when the user received the reminder, when the pressure relief exercise was completed, how many times the user was notified and completed pressure relief.

A clinician may, for example, recommend that a pressure relief maneuver should be done every 30 minutes. In that case, the application hereof may, for example, remind the user when 30 minutes have elapsed since the last effective pressure relief maneuver. If the user performs a forward lean, the application will compare the change in the center of pressure measurement to a threshold set by the clinician. When the lean exceeds the prescribed threshold, a separate timer or counter may begin counting, and alert the user when enough time has passed for the lean to be considered an effective pressure relief maneuver of event. The counter may, for example, be started when a value of the center of pressure indicates that one of a number of defined types of pressure relief had been initiated. The counter may, for example, be paused if the value of the center of pressure no longer indicates the pressure relief maneuver is being executed after a defined period of time. The counter may be restarted (further accumulating time for the event) if the value of the variable once again indicates the continuation of pressure relief maneuver within a second defined predetermined time. The counter may be stopped and reset to zero if the value of the center of pressure does not indicate restarting or continuance of the pressure relief maneuver within the second defined period of time. If it is determined, as described herein, that sufficient active seating by the user has occurred in the interim between a periodic reminder (for example, spaced in time by 30 minutes), a reminder may be canceled, thereby reducing the likelihood of disturbance of the user. A cumulative period of small movements may, for example, be determined to be an effective pressure relieve event in the interim between scheduled reminders.

Data from other subjects in the study of center of pressure changes while executing the same pressure relief maneuvers were found to be substantially equivalent. These findings suggest that it should be possible to construct a classification algorithm based on decision trees, or other similar machine learning techniques, that is capable of identifying and differentiating between different types of pressure relief maneuvers. The data and interpretation methods set forth above may further serve as the foundation for a machine learning algorithm, that can identify when a wheelchair user is attempting a pressure relief and determine the specific type of pressure relief maneuver being attempted. Such information is useful in building a coaching app for effective pressure relief behaviors.

As described above, a relationship between center of pressure and seated position was established for various types of pressure relief maneuvers, including, for example, left, right, and forward leaning pressure relief maneuvers. In a number of further studies, two clinicians classified a number of study participants as exhibiting active sitting/seating behavior or passive sitting/seating behavior. In that regard, some wheelchair users may not actually perform what clinicians may define as pressure relief or a predefined pressure relief maneuver. Such users may sometimes be considered as exhibiting or performing "active sitting", which means that the users shift their mass frequently without completely unweighting their buttocks or making large shifts in the center of pressure. The characteristics of the time series forces may be analyzed via one or more machine learning algorithms to predict "active sitting". In a number of studies, sixteen study participants were classified by the clinicians as exhibiting active sitting behavior, while thirteen were classified as exhibiting passive sitting behavior. An algorithm based on decision trees was developed to discriminate between the types of pressure relief.

Figure 9:
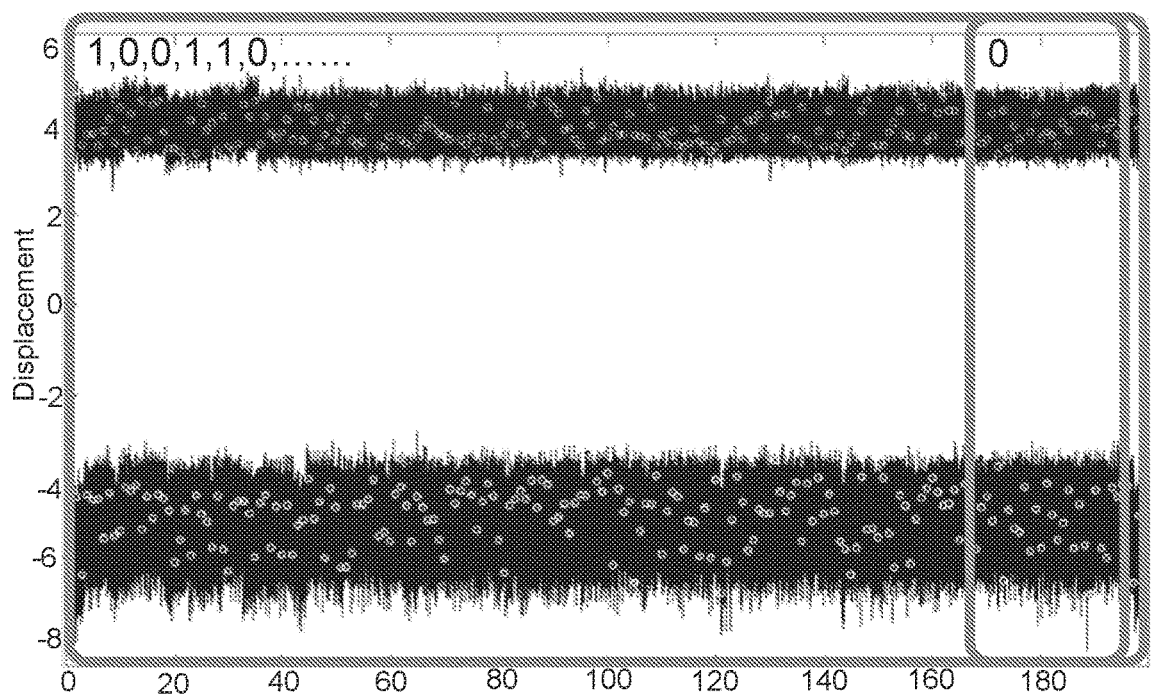
FIG. 9 illustrates center of pressure data collected for 200 seconds in a protocol study hereof, wherein the circles are down-sampled data.
Figure 10A:
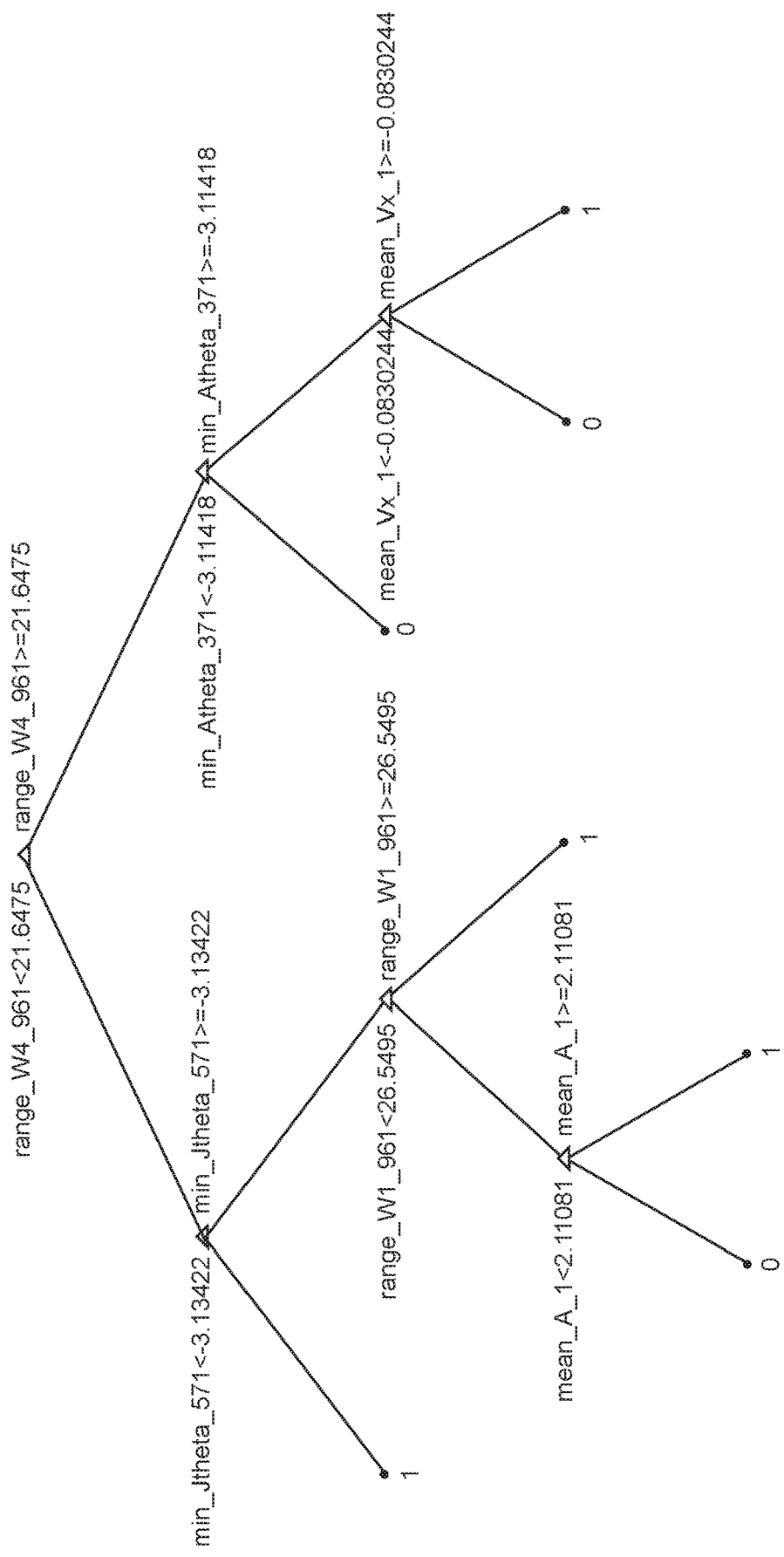
FIG. 10A illustrates an embodiment of a decision trees with 100% accuracy for determining active seating.

The collected sensor data were converted to center of pressure. The sampling rate was 1000 Hz. However, to establish a classifier for real-time use, the data were down-sampled to 1 Hz. As shown in FIG. 9, the top and bottom lines are the center of pressure data for 200 seconds and the circles are the down-sampled data. To provide sufficient samples for machine learning, various learning window sizes were tested: 2, 5, 10, 30, 60, 90, 120, 150, 180 seconds. Four machine learning algorithms were studied or tested to establish a machine learning classifier: complex decision tree, bagged decision tree, fine KNN (K nearest neighbors), and SVM (support vector machines). The sitting behaviors of the twenty-nine participants classified by the clinicians were used as the ground truth for training the classifier. The Fine KNN achieved 100% accuracy with a 5-second learning window and others achieved 100% with a 60-second learning window. A MatLab program was developed to down-sample center of pressure data, select data using learning window size, establish ground truth dataset, train machine learning classifier, test accuracy of classifiers, and classify sitting behaviors. In FIG. 9, the numerals "1,0,1,1, 0, . . . " are the classification results of active and passive seating behavior determined by the machine learning classifier. This classification is determined according to the down-sampled data within the rectangle shown in FIG. 9. Therefore, the classifier will generate a new result once receiving new data. This methodology provides continuous monitoring and recording when the user is sitting in the chair. FIG. 10A shows one example of the decision trees that achieved 100% accuracy. It used the weight range, jerk angle, mean acceleration, angle minimum, and x-axis velocity from the center of pressure data as inputs to the, above enumerated, machine learning algorithms to classify the sitting behavior.

As described above, the machine learning algorithms achieved 100% accuracy on the sitting behaviors of twenty-nine participants previously classified by clinicians. To further examine the difference between classifiers, the data of thirteen participants upon whom the clinicians had disagreements or whom the clinicians did not rate were classified with the four classifiers as shown in Table 1 of FIG. 10B. Most classifiers tended to rate as active, rather than as passive, but the SVM was less optimistic. Representative embodiments of the systems hereof may, for example, use multiple classifiers. In a number of embodiments in which multiple classifiers are use, if any of the classifiers identify the need to perform a pressure relief, the algorithm provides instruction to perform a pressure relief.

As the algorithms set forth in Table 1 of FIG. 10B provided the likeliness of active/passive sitting behavior, some participants were rated between 0 and 1, which is in concordance with the disagreement of the clinicians' judgment. This disagreement may arise because it is difficult to make clinical judgments on occasional active sitting actions. The classifiers showed the percentage of active sitting behavior during the testing period which may be used as a scoring system to help the user maintain healthier sitting behavior.

Data collected on wheelchair user seating actions may also be used to assess user discomfort related to the wheelchair sitting activity. A tool/application for determining user discomfort may, for example, be used to assess the user's wheelchair seating discomfort levels with seating repositioning (for example, as a function of seated time, movement of center of pressure, weight distribution, and frequency of pressure relief). A general discomfort score and a discomfort intensity score may, for example, be determined. See, for example, Crane BA, Holm MB, Hobson D, Cooper RA, Reed MP, Stadelmeier S, Responsiveness of the TAWC Tool for Assessing Wheelchair Discomfort, Disability and Rehabilitation: Assistive Technology, Vol. 2, No. 2, pp. 97-103, 2007, the disclosure of which is incorporated herein by reference. When, for example, a machine learning algorithm detects some combination of the above enumerated factors that may be related to sitting discomfort scores, the user can be alerted to adjust his/her position before reaching a state of discomfort.

Figure 11E:
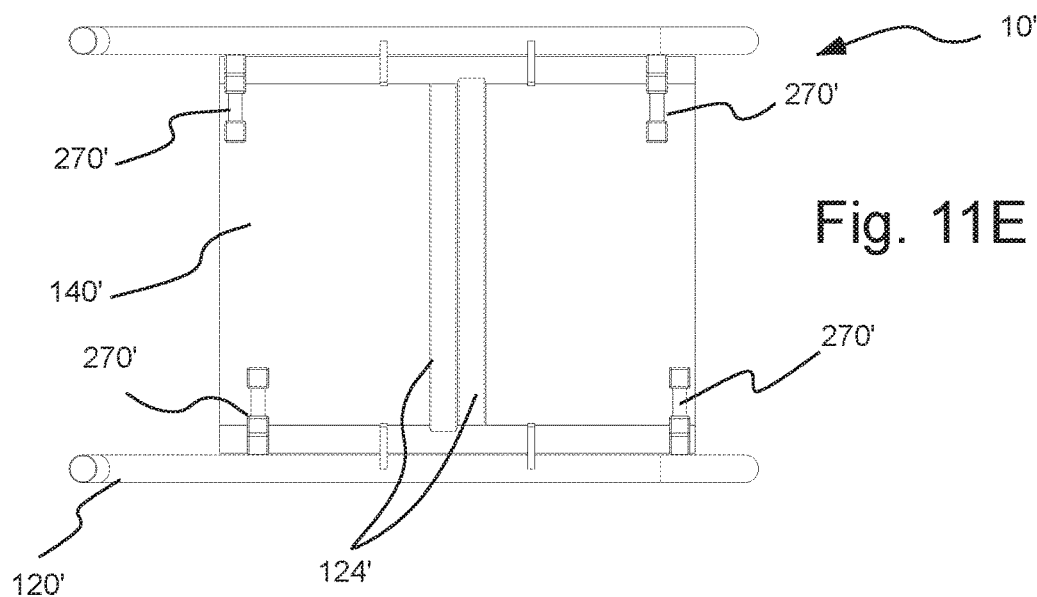
FIG. 11E illustrates a bottom view of the frame of FIG. 11A in an extended state.
Figure 11F:
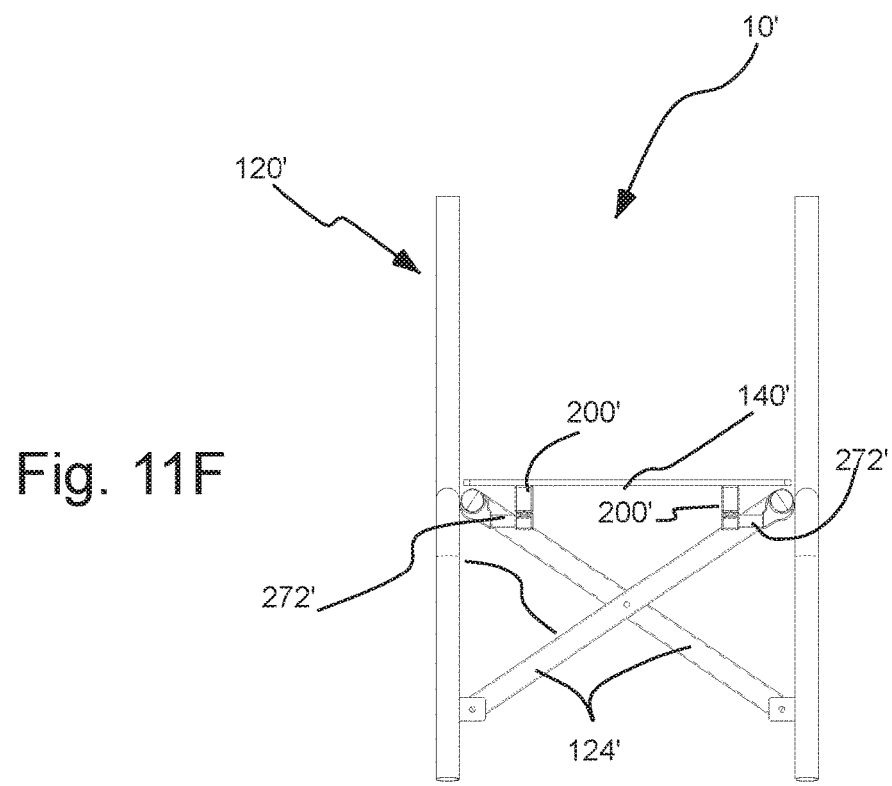
FIG. 11F illustrates a front view of the frame of FIG. 11A in an extended state.

The force sensors systems and algorithms/applications hereof may be used in connection with almost any type of manual wheelchair. FIGS. 11A through 11F, for example, illustrate another embodiment of a system 10, hereof including a wheelchair (not shown in its entirety but similar to wheelchair 100). The wheelchair includes a frame 120' and a plurality of wheels (not shown, but similar to manually powered rear wheels 132 and front caster wheels 134 of wheelchair 100) attached to frame 120. Frame 120' is foldable as illustrated, for example, in FIG. 11A via frame cross members 124', which are rotatably or pivotably attached to each other at a pivot point P (see FIG. 11B) as known in the foldable wheelchair arts. The wheelchair further includes a rigid seat pan 140', which is removable to enable folding of the wheelchair as illustrated in FIG. 11A.

A force sensor system, arrangement or array for the wheelchair includes a plurality of force sensors that are placed in operative contact or connection with a bottom surface of rigid seat pan 140'. As described above in connection with system 10' each of the plurality of force sensors is positioned at a different, unique position with respect to frame 120' and to rigid seat pan 140' to define a measurement plane or array. In the illustrated embodiment, four force sensors 200' are illustrated. In the illustrated embodiment rigid seat pan 140' is connected and supported by each of the plurality of sensors 200 at different positions on rigid seat pan 140' so that the rigid seat pan 140' does not contact frame 120' other than via sensor 200 and an associated support member 270', which is attached to frame 120'. In number of embodiments, each of forces sensors 200' includes at least one strain gauge. In the illustrated embodiment of FIGS. 11A through 11F, each of force sensors 200 is independently connected to frame 120' via an independent and separate associated support member 270'. As illustrated in, for example, FIG. 11C each sensor 200 may include a connector 205' which forms a connection with a cooperating connector 272' of associated support member 270' (for example, a dovetail connector and a cooperating dovetail slot).

Parameters for determining information to a user such as reminders and/or other instructions hereof may, for example, be personalized according to individual needs. Moreover, data from usage of the systems hereof (for a single user and/or over multiple users) may be used to personalize parameters or settings for a particular user. In a number of embodiments, the systems are attachable to wheelchairs and are quite simple to install. The systems hereof can readily be installed on virtually any manual wheelchairs, including by retrofitting. Moreover, the user interface is user-friendly and may be incorporated into, for example, regular smartphone usage. In addition to reminding wheelchair users to perform appropriate repositioning their seating for health management, the systems hereof may also monitor seating activity to improve safety.

The real time usage reminders from the systems hereof may, for example, instruct users to adjust the seating position based on clinical recommendations and environmental settings/conditions, which may, for example, extend training beyond the clinical setting. In addition, with periodic seating repositioning or pressure relief maneuver instructions, users may follow the instruction to perform an effective pressure relief maneuver to reduce the risk of, for example, developing pressure sores, minimize fatigue and/or pain, and decrease edema in lower limbs. Moreover, clinicians are able to provide personalized health education and coaching by customizing the feedback of the systems hereof for each manual wheelchair user. A clinician or other authorized person can, for example, access systems hereof remotely (if, for example, allowed/enabled by a user) via the communication system (for example, as integrated within a personal communication device) to, for example, modify one or more parameters or settings. For example, the frequency of reminders, various thresholds in the center of pressure associated with types of pressure relief and/or the time required to achieve an effective pressure relief maneuver may be adjusted for a particular user. Moreover, a technician may be able to review data remotely to schedule maintenance.

In a number of embodiments, the systems hereof 1) determine the need for a reminder and the timing thereof, 2) remind/inform a user about the time to perform repositioning; 3) provide real time audio, visual, audio-visual/video and/or tactile feedback to guide the users regarding, for example, a particular pressure relief maneuver; and 4) provide real time audio, visual, audio-visual and/or tactile feedback to guide the users to stay in a seating position for a desired duration, and 5) confirm the effective achievement or completion of pressure relief maneuver. Clinicians may recommend active seating regimes based on individual needs and preference. The user may also set or adjust parameters/settings. The parameters/settings of the devices, systems and methods hereof may thus be partially or completely customizable for each user.

A location sensor or system (for example, using a global position system or GPS) of, for example, smartphone 500 may, for example, enable communication/interaction with one or more information databases (for example, a web-based information database) so that information related to position/location (such as information regarding a path that the wheelchair is travelling) can be incorporated into determining safe ranges of settings and/or contextual awareness. A pathway measurement/characterization tool and database for defining pathway condition/roughness is, for example, disclosed in U.S. Pat. No. 10,101,454, the disclosure of which is incorporated herein by reference. Moreover, various sensors such as GPS, differential GPS. microphones, light sensors, and internal measurement unit (IMU) sensors, location sensors, sound level sensors, setting sensors and situation sensors may be included in systems hereof. Using predetermined rules and, in some embodiments, machine learning algorithms, data from such sensors may, for example, assist in estimating or determining the location of a wheelchair user as well as the nature of an activity in which the user is partaking (for example, if the user is in a crowded room, outdoors, in a meeting). The user may also determine how information (for example, alerts or reminders) is communicated by, for example, placing a phone ring on silent etc. Settings and parameters of the systems hereof may, for example, be dependent upon the circumstances or context of the user's surroundings and/or activities. In that regard, data from such sensors may be used to tailor how the systems hereof communicates with the user. For example, if it is determined from, for example, location, sound levels, lighting (indoor lights have a predictable signal) etc., that the user is in an indoor meeting, feedback to the user may be tailored to the determined "context". The user may, for example, be prompted to confirm a determination of location/activity. Furthermore, GPS and/or microphones (sound/pressure sensors) can determine whether the wheelchair user is close to a busy street, or the microphones can infer that the user is in a crowd, and may not wish to be reminded of a propulsion technique, safety (e.g., seated stability, functional reach), pressure relief or for body mass maintenance or loss at that time. Parameters for the effect of context may be tailored for an individual user by, for example, a clinician and/or the user.

In a number of representative embodiments, data is processed, and information is provided to the wheelchair user (and communicated to one or more remote systems), at least in part, via a personal communication device. However such functions may be carried out (in whole or in part) via systems in operative connection with, embedded within, or integrated with a wheelchair. For example, the onboard electronic circuitry and onboard sensors of a manual wheelchair hereof may be configured to provide functionality as described herein, and a robust communication system may be integrated or operatively connected with the onboard electronic circuitry. Likewise, such functionality may be distributed between systems integrated with wheelchair and, for example, another system such as a personal communications device and/or a remote system which may be placed in operative/communicative connection with the wheelchair. The use of personal communication devices for processing power, interfacing with a user and communications may, for example, provide one manner of readily retrofitting existing wheelchairs to provide devices, systems and methods hereof.

In a number of embodiments, a first software program in the form of a first app or application installed on smartphone 500 (or other personal communication system) processes the sensor data (for example, collected by sensors 200 and/or other sensors hereof). A second software program in the form of a second app (sometimes referred to herein as a coaching app) installed on smartphone 500 executes a coaching algorithm, which, for example, determine a message/instruction and then displays the coaching message on smartphone display 510 to guide the user to perform repositioning. The first app and the second app may be downloadable to the mobile personal communication device in a manner known in the personal communication device arts. The second app may also do one or more of the following: display real time visual and/or audio feedback to the user, store data, generate usage profile/reports (for example, with charts and stats summary for future review), and send data and/or reports to, for example, a clinician under the user's permission. The functions of the first app and second app as described above may, for example, be integrated into a single application or distributed over any number of applications.

Reports may, for example, include user seating activity history over time. Compliance with, for example, pressure relief reminders may be tracked with categories of response such as reminder ignored, reminder dismissed, and pressure relief recommendation completed. Similarly compliance with safety warnings may be tracked. The number of times such actions are taken over a period of time (for example, one day or 24 hours) may be tracked. A number of variables may be reported for clinical interpretation. Such variables may, for example, include wheelchair occupancy time (for example, as determined using detection of weight via sensors 200) and driving distance (for example, as determined via accelerometer data or one or more wheel encoders).

Because system 10 may include telephone connectivity as, for example, provided by a personal communication device (for example, a cell phone/smartphone), system 10 is readily used as a component of, for example, a tele-health system or tele-rehab system. In that regard, as described above, data can be readily and easily communicated to clinicians. Long term health and/or recovery may, for example, be monitored. Data may, for example, be uploaded to a cloud-based system (for example, to a drop box) or via email. System 10 may, for example, provide for modifiable settings or parameters (for example, time and frequency) for email transmission or data upload. Data may, for example, be processed as described in US Patent Publication No. 2015/0209207.

Using web-based or cloud based communications between system 10 and, for example, a clinician, the clinician may be provided the ability to change guidelines or settings in system 10 remotely. System 10 may, for example, interact with various platforms such as the Interactive Mobile Health & Rehabilitation (iMHere) described, for example, in Pannanta B. et al "iMHere: A Novel mHealth System for Supporting Self-Care in Management of Complex and Chronic Conditions." JMIR Mhealth and Uhealth 1 (2) (July 11): e10. doi:10.2196/mhealth.2391 (2013), to provide clinician communication. The iMHere platform provides clinician guided self-care to patients with chronic issues. The platform connects patient apps with a web-based clinician portal over a secure two-way Internet bridge. The user's medical records may, for example, be accessed and data from system 10 may be entered in such records. Moreover, the user's medical records can be used to change system 10.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A wheelchair system, comprising:
a wheelchair comprising a frame, a plurality of wheels attached to the frame; a sensor system comprising a plurality of force sensors, the plurality of force sensors comprising at least three force sensors, each of the plurality of force sensors being attached to the frame and being positioned at a different position; and a rigid seat pan placed in contact with each of the plurality of force sensors at a different position on the rigid seat pan so that the rigid seat pan does not contact the frame and forces on the rigid seat pan are transferred to the plurality of force sensors;
a processor system, each of the plurality of force sensors being in communicative connection with the processor system,
a memory system in communicative connection with the processor system,
a user interface system in communicative connection with the processor system, and instructions on the memory system which are executable by the processor system to determine a value of a variable related to a distribution of force on the rigid seat pan and thereby seating position of a user on a seat operatively connected to the rigid seat pan over time from data from each of the plurality of force sensors.

2. The wheelchair system of claim 1 wherein the memory system further includes instructions executable by the processor system to provide information via the user interface system to a user of the wheelchair based upon the distribution of force on the rigid seat pan over time to assist the user to adjust the seating position of the user in accordance with parameters stored in the memory system.

3. The wheelchair system of claim 2 wherein the sensor system comprises at least four force sensors.

4. The wheelchair system of claim 3 wherein each of the at least four force sensors comprises at least one strain gauge.

5. The wheelchair system of claim 3 wherein each of the at least four force sensors measures tensile and compressive forces.

6. The wheelchair system of claim 3 wherein the variable is a center of pressure or force on the rigid seat pan.

7. The wheelchair system of claim 6 wherein a total force on the rigid seat pan is determined and used in determining at least one type of pressure relief.

8. The wheelchair system of claim 6 wherein an effective pressure relief event is determined to have been achieved if a predetermined cumulative period of time that the value of the variable indicates at least one the type of pressure relief is achieved.

9. The wheelchair system of claim 8 wherein the user is notified via the user interface system if the effective pressure relief event is achieved.

10. A wheelchair system, comprising:
a wheelchair comprising a frame, a plurality of wheels attached to the frame: a sensor system comprising a plurality of force sensors, the plurality of force sensors comprising at least four force sensors. each of the plurality of force sensors being attached to the frame and being positioned at a different position; and a rigid seat pan placed in contact with each of the plurality of force sensors at a different position on the rigid seat pan so that the rigid seat pan does not contact the frame and forces on the rigid seat pan are transferred to the plurality of force sensors;
a pedestal connected to the frame and a support structure connected to the pedestal, each of the at least four force sensors being attached to the support structure;
a processor system, each of the plurality of force sensors being in communicative connection with the processor system,
a memory system in communicative connection with the processor system,
a user interface system in communicative connection with the processor system, and
instructions on the memory system which are executable by the processor system to determine a value of a variable related to a distribution of force on the rigid seat pan over time and to provide information via the user interface system to a user of the wheelchair based upon the distribution of force on the rigid seat pan over time to assist the user to adjust a seating position of the user in accordance with parameters stored in the memory system.

11. The wheelchair system of claim 10 wherein the support structure includes four radially outward extending members and each one of the at least four force sensors is attached to a different one of the radially outward extending members.

12. The wheelchair system of claim 3 wherein each of the four force sensors is independently connected to the frame.

13. The wheelchair system of claim 2 wherein the memory system comprises readable instructions that are executable by the processor system to provide user instructions to the user to adjust seating position of the user to perform pressure relief in accordance with parameters stored in the memory system.

14. The wheelchair system of claim 13 wherein the processor system is configured to store data regarding at least one of a user instruction or a user action in the memory system.

15. The wheelchair system of claim 13 wherein the processor system monitors to determine if an effective pressure relieve event has occurred.

16. The wheelchair system of claim 13 further comprising a communication system in operative connection with the processor system, wherein data is transmitted to a remote system via the communication system or data is received from the remote system.

17. The wheelchair system of claim 13 wherein the user interface system comprises a display.

18. The wheelchair system of claim 13 further comprising a communication system in operative connection with the processor system, and wherein at least one processor of the processor system, at least one memory component of the memory system, at least one communication component of the communication system or at least one interface component of the interface system are provided by a personal communication device.

19. The wheelchair system of claim 18 wherein the personal communication device is a smartphone or a tablet computer.

20. The wheelchair system of claim 13 wherein the wheelchair is a manually powered wheelchair.

21. The wheelchair system of claim 2 wherein the processor system provides information via the user interface system to a user of the wheelchair based upon the distribution of force on the rigid seat pan over time regarding seating posture of the user.

22. The wheelchair system of claim 21 wherein instructions are provided to the user to assist the user to adjust the seating posture of the user in accordance with parameters stored in the memory system.

23. A method of tracking seating activity of a user in a wheelchair system including a wheelchair including a frame, a plurality of wheels attached to the frame and a rigid seat pan, comprising:
providing a sensor system comprising a plurality of force sensors, the plurality of force sensors comprising at least three force sensors, each of the plurality of force sensors being attached to the frame and being positioned at a different position relative to the frame, the rigid seat pan being placed in contact with each of the plurality of force sensors at a different position on the rigid seat pan so that the rigid seat pan does not contact the frame and forces on the rigid seat pan are transferred to the plurality of force sensors;
providing a processor system, each of the plurality of force sensors being in communicative connection with the processor system,
providing a memory system in communicative connection with the processor system, and executing instructions stored on the memory system via the processor system to determine a value of a variable related to a distribution of force on the rigid seat pan and thereby seating position of a user on a seat operatively connected to the rigid seat pan over time from data from each of the plurality of force sensors.

24. A method of providing information regarding seating activity to a user of a wheelchair including a frame, a plurality of wheels attached to the frame and a rigid seat pan, comprising:

providing a sensor system comprising a plurality of force sensors, the plurality of force sensors comprising at least three force sensors, each of the plurality of force sensors being attached to the frame and being positioned at a different position, the rigid seat pan being placed in contact with each of the plurality of force sensors at a different position on the rigid seat pan so that the rigid seat pan does not contact the frame and forces on the rigid seat pan are transferred to the plurality of force sensors;

providing a processor system, each of the plurality of force sensors being in communicative connection with the processor system, providing a memory system in communicative connection with the processor system, providing a user interface system in communicative connection with the processor system, executing instructions stored on the memory system via the processor system to determine a value of a variable related to a distribution of force on the rigid seat pan and thereby seating position of a user on a seat operatively connected to the rigid seat pan over time from data from each of the plurality of force sensors; and providing information via the user interface system to a user of the wheelchair based upon the distribution of force on the rigid seat pan over time to assist the user to adjust a seating position of the user in accordance with parameters stored in the memory system.

* * * * *